United States Patent [19]

Narisada et al.

[11] Patent Number: 4,916,231

[45] Date of Patent: Apr. 10, 1990

[54] ALKENYLTETRAZOLE DERIVATIVES

[75] Inventors: Masayuki Narisada, Osaka; Mitsuaki Ohtani; Fumihiko Watanabe, both of Nara; Takaharu Matsuura, Hyogo; Sanji Hagishita, Nara; Kaoru Seno, Hyogo, all of Japan

[73] Assignee: Shionogi & Co., Ltd., Osaka, Japan

[21] Appl. No.: 377,409

[22] Filed: Jul. 10, 1989

[30] Foreign Application Priority Data

Jul. 19, 1988 [JP] Japan .................. 63-181274
Mar. 7, 1989 [JP] Japan .................. 64-54569

[51] Int. Cl.$^4$ ............................ C07D 409/08
[52] U.S. Cl. ........................ 548/252; 548/253
[58] Field of Search ........................ 548/252, 253

[56] References Cited

U.S. PATENT DOCUMENTS 4,670,453 6/1987 Das .................. 548/253
4,749,715 6/1988 Hall .................. 548/253

Primary Examiner—David B. Springer
Attorney, Agent, or Firm—Wenderoth, Lind & Ponack

[57] ABSTRACT

Tetrazole derivatives represented by the formula:

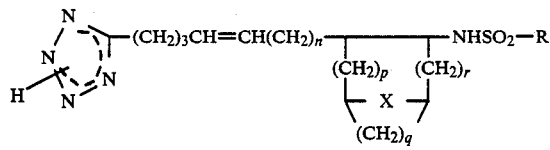

wherein R is naphthyl or phenyl optionally substituted by phenyl, lower alkyo, halogen, lower alkoxy, hydroxy or acetoxy; X is methylene, dimethylmethylene or oxygen; n is an integer of 0 or 1; and p and r each is an integer of 0 or 1 and q is an integer of 1 or 2 provided that $p+q+r=2$; or a tautomer in tetrazole ring and a pharmaceutically acceptable salt thereof, which are useful as $TXA_2$ receptor antagonist.

5 Claims, No Drawings

ALKENYLTETRAZOLE DERIVATIVES

BACKGROUND OF THE INVENTION

1. Field of the Invention

This invention relates to substituted alkenyltetrazole derivatives which are used in the field of the medicine for improving by decreasing the symptoms caused by thromboxane. Concretely speaking, this invention relates to substituted bicycloheptylalkenyltetrazole derivatives or a pharmaceutically acceptable salt thereof which are useful as antithrombotic, antivasoconstricting, and anti-bronchoconstricting drugs.

2. Description of the Prior Art

The general course of atherosclerosis, which is regarded as the main risk factor of myocardial infarction and cerebral infarct, begins in the arterial intima with mucoid accumulation and fibroblast formation, progressively followed by degeneration, lipid and cholesterol deposition, and destruction and atheromasia of the intima tissue, with gradual formation of high-degree and localized hypertrophy in the intima. The atherosclerosis has long been regarded to be caused by thrombus formation and fibrin deposition, but recent discoveries of thromboxane $A_2$ ($TXA_2$) by Samuelsson et al. and prostacyclin ($PGI_2$) by Vane et al. have revealed an interaction between platelets and vessel wall. Platelets are said to play an important role in the onset and progress of atherosclerosis. Therefore, it is now recognized that the use of antithrombotic drugs, particularly drugs which inhibits platelet aggregation, are effective for the treatment of atherosclerotic diseases.

In addition to the conventional antithrombotic drugs such as heparin and coumarin compounds, certain types of prostaglandins are known to have a potent platelet aggregation inhibitory action. From these facts, prostaglandin derivatives have attracted much attention as possible antithrombotic drugs. For example, analogues of Prostaglandin $E_1$ and $I_2$ receptor agonists have been developed. Since thromboxane $A_2$ shows potent platelet aggregation and vasoconstriction action, thromboxane $A_2$ synthesis inhibitors, such as cyclooxygenase inhibitors and thromboxane synthetase inhibitors, and thromboxane $A_2$ receptor antagonists, have been developed. The thromboxane $A_2$ receptor antagonists include 13-APA [Venton D.L. et al., J. Med. Chem., 22, 824 (1979)], $PTA_2$ [Lefer A.M. et al., Proc. Natl. Acad. Sci. U.S.A., 76, 2566, (1979)], BM-13177 [Lefer A.M. et al., Drugs of Today, 21, 283 (1985)], SQ-29548 [Ogletree et al., J. Pharmacol. Exp. Ther., 34, 435 (1985)], and the like. Japan Kokai Patent Publication No. 88-139161 and U.S. Patent No. 4654375 also include the compound of this type. The tetrazole derivatives of physiologically active carboxylic acids of these kind are disclosed in J. Med. Chem., 22, 1340, (1979) or the like.

When thrombin acts on platelets, cyclooxygenase is activated. By activation of cyclooxygenease, thromboxane $A_2$ is produced enzymatically in platelets, vessel wall, and various other cells, from arachidonic acid through prostaglandins $G_2$ and $H_2$. This product has various potent physiologic or pathogenic actions. In particular, the potent platelet aggregation action and the action constricting the smooth muscle of bronchi and of coronary, cerebral, and pulmonary arteries, etc. are considered to be the factors which relate to the onset and progress of such circulatory and respiratory diseases as angina pectoris, myocardial infarction, cerebral infarction, and bronchial asthma. Moreover, it is said that the strong action occurs even at a concentration of $10^{-10} - 10^{-11}M$. Therefore, increasing attention has been paid to the development of thromboxane $A_2$ antagonists or inhibitors as anti-thrombotics, anti-vasoconstrictives or anti-bronchoconstrictives. Inhibitors, however, have some problems in view of the fact that they influence on prostaglandins which bear various important roles as well as thromboxane $A_2$, and uncontrolled thromboxane-like harmful effects are caused by accumulated substrates. So, development of receptor antagonists has especially been sought. However, this kind of antagonist has some problems, e.g., short action, emergence of partial agonistic action, hardness to separate traget effect from potential effects, or the like.

Summary

Tetrazole derivatives represented by the formula (I):

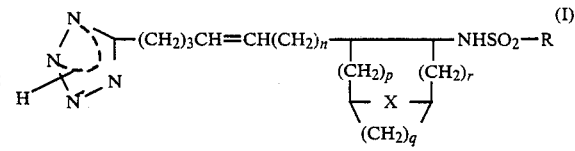

wherein R is naphthyl or phenyl optionally substituted by phenyl, lower alkyl, halogen, lower alkoxy, hydroxy or acetoxy; X is methylene, dimethylmethylene or oxygen; n is an integer of 0 or 1; and p and r each is an integer of 0 or 1 and q is an integer of 1 or 2 provided that $p+q+r=2$, their tautomers in tetrazole ring, and pharmaceutically acceptable salts thereof.

These compounds may be useful as $TXA_2$ receptor antagonist, e.g., antithrombotic, anti-vasoconstricting, and anti-bronchoconstricting drugs.

DESCRIPTION OF THE PREFERRED EMBODIMENT

The inventors have succeeded in preparing substituted alkenyltetrazole derivatives of the formula (I):

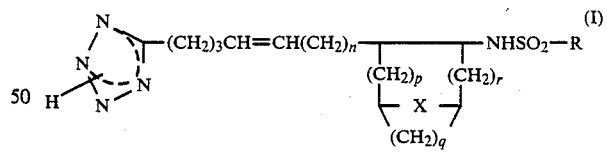

wherein R is naphthyl or phenyl optionally substituted by phenyl, lower alkyl, halogen, lower alkoxy, hydroxy or acetoxy; X is methylene, dimethylmethylene or oxygen; n is an integer of 0 or 1; and p and r each is an integer of 0 or 1 and q is an integer of 1 or 2 provided that $p+q+r=2$;

their tautomers in tetrazole ring and pharmaceutically acceptable salts thereof, and found that these new compounds have potent activity as thromboxane $A_2$ receptor antagonists which are stable chemically and biochemically. The present invention is based on these findings.

The tautomers in tetrazole ring means 1H-tetrazol-5-yl and 2H-tetrazol-5-yl as shown below.

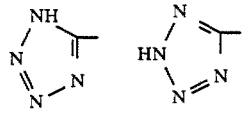

In the following reaction scheme and examples, the tautomers in tetrazole ring are described in a single formula as shown below in order to represent both 1H-tetrazol-5-yl and 2H-tetrazol-5-yl.

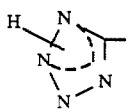

The following definitions are given for various terms used throughout this specification.

The term "lower alkyl" includes straight or branched $C_1$ and $C_7$ alkyl, e.g., methyl, ethyl, n-propyl, isopropyl, diisopropylmethyl, butyl, isobutyl, tert-butyl, pentyl, hexyl, heptyl, or the like.

The term "lower alkoxy" includes straight or branched $C_1$ to $C_7$ alkoxy, e.g., methoxy, ethoxy, propoxy, isopropoxy, butoxy, isobutoxy, tert-butoxy, pentoxy, hexyloxy, heptyloxy, or the like.

The term "halogen" includes chlorine, bromine, iodine, and fluorine.

In the general formula (I), preferable R includes 2-naphthyl, unsubstituted phenyl, substituted phenyl which has one or more substituents, e.g., lower alkyl, halogen, lower alkoxy, hydroxy, acetoxy, phenyl, or the like at any possible position, i.e., 2-, 3-, 4-, 5-, and/or 6-. Representatives of the substituted phenyl are, for example, lower alkylphenyl (e.g., m-tolyl, p- tolyl, 3-ethylphenyl, 4-ethylphenyl, 4-isopropylphenyl, 4-tert-butylphenyl, or the like), lower alkoxyphenyl (e.g., 4-methoxyphenyl, 4-ethoxyphenyl, 4-isopropoxyphenyl, or the like), halophenyl (e.g., 2-chlorophenyl, 3-chlorophenyl, 4-chlorophenyl, 2-bromophenyl, 3-bromophenyl, 4-bromophenyl, 4-iodophenyl, or the like), 4-hydroxyphenyl, biphenylyl, or the like. Amongst them, p-tolyl, 2-chlorophenyl, 3-chlorophenyl, 4-bromophenyl, 4-hydroxyphenyl, 4-acetoxyphenyl, 4-methoxyphenyl, biphenylyl, or the like is preferable.

According to the present inventors' study, unsubstituted phenyl or phenyl substituted by lower alkyl, halogen, lower alkoxy, hydroxy, acetoxy, or phenyl at 4 position is especially preferred.

The preferable combinations of X and n, p, q, and r are: when X is methylene, n is 0 or 1, p is 0, q is 2, and r is 0; when X is dimethylmethylene, n is 1, p is 0 or 1, q is 2, and r is 0 or 1; and when X is oxygen, n is 1, p is 0, q is 2, and r is 0.

Some representatives of the compounds (I) are shown below but are not intended to limit the scope of the present invention.

(1R,2S,3S,4S)-2-[(2Z)-6-(5-tetrazolyl)hex-2-enyl]-3-(4-tolylsulfonylamino) bicyclo[2.2.1]heptane, (1R,2S,3S,4S)-3-(4-bromophenylsulfonylamino-2-[(2Z)-6-(5-tetrazolyl) hex-2-enyl]bicyclo[2.2.1]heptane, (1R,2S,3S,4S)-3-(4-hydroxyphenylsulfonylamino)-2-[(2Z)-6-(5-tetrazolyl) hex-2-enyl]bicyclo[2.2.1]heptane, (1R,2S,3S,4S)-3-(4-methoxyphenylsulfonylamino)-2-[(2Z)-6-(5-tetrazolyl) hex-2-enyl]bicyclo[2.2.1]heptane, (1R,2S,3S,4S)-3-phenylsulfonylamino-2-[(2Z)-6-(5-tetrazolyl) hex-2-enyl]bicyclo[2.2.1]heptane, (1R,2R,3S,4S)-3-phenylsulfonylamino-2-[(1Z)-5-(5-tetrazolyl) pent-1-enyl]bicyclo[2.2.1]heptane, (1R,2R,3S,4S)-3-(4-bromophenylsulfonylamino)-2-[(1Z)-5-(5-tetrazolyl) pent-1-enyl]bicyclo[2.2.1]heptane, (1R,2R,3R,4S)-3-phenylsulfonylamino-2-[(2Z)-6-(5-tetrazolyl) hex-2-enyl]-7-oxabicyclo[2.2.1]heptane, (1R,2S,3S,4S)-3-phenylsulfonylamino-2-[(2Z)-6-(5-tetrazolyl) hex-2-enyl]-7-oxabicyclo[2.2.1]heptane, (1S,2S,3S,5R)-3-phenylsulfonylamino-2-[(2Z)-6-(5-tetrazolyl) hex-2-enyl]-6,6-dimethylbicyclo[3.1.1]heptane, (1S,2R,3S,5S)-2-phenylsulfonylamino-3-[(2Z)-6-(5-tetrazolyl) hex-2-enyl]-6,6-dimethylbicyclo[3.1.1]heptane, (1S,2R,3S,5S)-2-[(4-biphenylyl)sulfonylamino]-3-[(2Z)-6-(5-tetrazolyl) hex-2-enyl]-6,6-dimethylbicyclo[3.1.1]heptane, (1S,2R,3S,5S)-2-[(2-naphthyl)sulfonylamino]-3-[(2Z)-6-(5-tetrazolyl) hex-2-enyl]-6,6-dimethylbicyclo[3.1.1]heptane, (1S,2R,3S,5S)-2-[(4-methoxyphenyl)sulfonylamino]-3-[(2Z)-6-(5-tetrazolyl) hex-2-enyl]-6,6-dimethylbicyclo[3.1.1]heptane, (1S,2R,3S,5S)-2-[(4-chlorophenyl)sulfonylamino]-3-[(2Z)-6-(5-tetrazolyl) hex-2-enyl]-6,6-dimethylbicyclo[3.1.1]heptane, (1S,2R,3S,5S)-2-[(3-chlorophenyl)sulfonylamino]-3-[(2Z)-6-(5-tetrazolyl) hex-2-enyl]-6,6-dimethylbicyclo[3.1.1]heptane, (1S,2R,3S,5S)-2-[(2-chlorophenyl)sulfonylamino]-3-[(2Z)-6-(5-tetrazolyl) hex-2-enyl]-6,6-dimethylbicyclo[3.1.1]heptane, (1S,2R,3S,5S)-2-(p-tolylphenylsulfonylamino)-3-[(2Z)-6-(5-tetrazolyl) hex-2-enyl]-6,6-dimethylbicyclo[3.1.1]heptane, and (1S,2R,3S,5S)-2-[(4-bromophenyl)sulfonylamino]-3-[(2Z)-6-(5-tetrazolyl) hex-2-enyl]-6,6-dimethylbicyclo[3.1.1]heptane.

The present invention involves every stereoisomer thereof (e.g., enantiomer and diastereoisomer) and the mixture thereof.

The pharmaceutically acceptable salts of the compounds (I) include, for example, salts with alkaline metal e.g., lithium, sodium, potassium, and the like, salts with alkaline earth metal e.g., calcium, magnesium, and the like, salts with organic base e.g., triethylamine, 2-aminobutane, tert-butylamine, diisopropylethylamine, n-butylmethylamine, n-butyldimethylamine, tri-n-butylamine, dicyclohexylamine, N-isopropylcyclohexylamine, furfurylamine, benzylamine, methylbenzylamine, diphenylamine, N,N-dimethylbenzylamine, 2-chlorobenzylamine, 4-methoxybenzylamine, 1-naphthylmethylamine, diphenylbenzylamine, triphenylamine, 1-naphthylamine, 1-aminoanthracene, 2-aminoanthracene, dehydroabiethylamine, N-methylmorpholine, pyridine, and the like, and salts with amino acid, e.g., lysine, arginine, histidine and the like.

The compounds of the present invention represented by the general formula (I) include all of the possible stereoisomeric forms (e.g., diastereomer, epimer, enantiomer, and the like).

The compounds of the present invention can be prepared from the compounds disclosed in Japan Kokai Patent Publication No. 63-139161, Japane Patent Application No. 63-105582, or the like as starting materials.

When the optically active compounds are used as the starting material, the compounds of the present invention can be prepared as the optically active compounds and when the racemates are used as the starting material, the compounds of the present invention can be pepared as the recemates. The optically active compounds may be also prepared from the racemate of the present invention by a conventional optical resolution technique or by asymmetric synthesis shown in the following Examples.

In this step, the compound II' is converted into the corresponding sulfonamide derivative I.

The reaction may be carried out using an arylsulfonyl halogenide such as 2-naphtylsulfonyl chloride, 4-biphenylylsulfonyl chloride, phenylsulfonyl chloride, alkoxyphenylsulfonyl chloride (4-methoxyphenylsulfonyl chloride, 4-ethoxyphenylsulfonyl chloride), alkylphenylsulfonyl chloride, (p-toluenesulfonyl chloride, 4-ethylphenylsulfonyl chloride), halophenylsulfonyl chloride (2-chlorophenylsulfonyl chloride, 3-chlorophenylsulfonyl chloride, 4-chlorophenylsulfonyl chloride, 4-bromophenylsulfonyl chloride, 4-fluorophenylsulfonyl chloride), 4-acetoxyphenylsulfonyl chloride, or the like in the presence of a base (e.g., pyridine, triethyl- Reaction Scheme (Route 1)

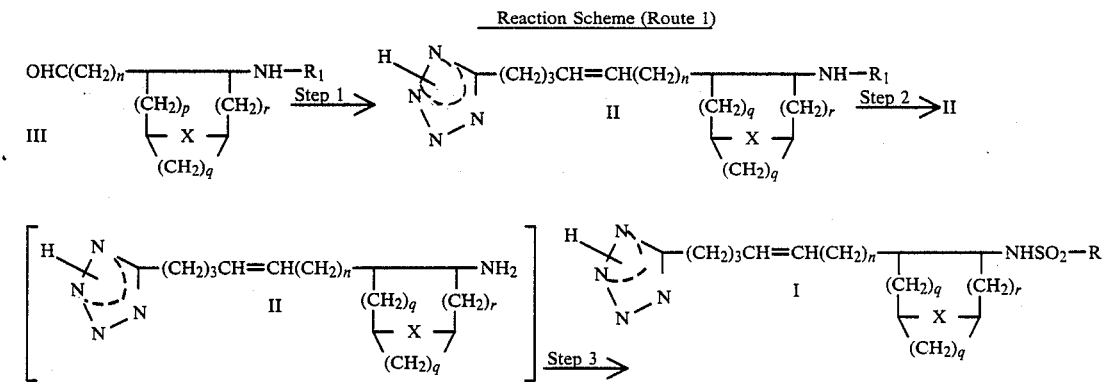

wherein $R_1$ is amino protecting group; R, n, p, q, and r each is the same as defined above.

In the reaction scheme, each definition of R, X, n, p, q, and r is the same as defined above.

$R_1$ is commonly used amino protecting group such as acyl (e.g., trifluoroacetyl), lower alkoxycarbonyl (e.g., tert-butoxycarbonyl, aryloxycarbonyl (e.g., benzyloxycarbonyl), or the like.

(Step 1)

In this step, an ylide is condensed to the compound III to give the compound II.

This step can be carried out according to a usual method of Wittig reaction.

The ylide used in this step can be prepared by the treatment of triphenyl[4-(5-tetrazolyl)butyl]phosphonium bromide [J. Med. Chem., 22, 1340 (1979)] with a base (e.g., sodium hydroxide, n-butyl lithium, potassium tert-butoxide, sodium dymsyl, potassium dymsyl).

The reaction is carried out in a solvent such as ether (e.g., diethyl ether, tertahydrofuran), n-hexane, dimethyl sulfoxide, or the like under heating or at room temperature for several hours.

(Step 2)

In this step, an amino protecting group (e.g., trifluoroacetyl, tert-butoxycarbonyl, benzyloxycarbonyl) of the compound II is removed to give the compound II'.

This step can be carried out by usual method to remove amino protecting group, for example, hydrolysis with an acid (e.g., sulfuric acid), or a base (e.g., sodium hydroxide, potassium hydroxide, barium hydoxide), treatment with trifluoroacetic acid and anisole, or the like. Though the resulting ammonium salt of compound II' can be used for next step, it may be converted into its free amine, if necessary, by treating with a base such as sodium carbonate, sodium hydrogencarbonate, or the like.

(Step 3)

amine) in a solvent such as chlorinated hydrocarbon (e.g., chloroform, dichloromethane), ether (e.g., diethyl ether, tetrahydrofuran), aromatic hydrocarbon (e.g., benzene), or the like at room temperature for several ten minutes. If necessary, 4-aminopyridine may be added as a catalyst. By this reaction, the compounds of the present invention are prepared.

The tetrazole derivatives prepared by this reaction can be converted into their desired salt by treating with alkai metal, or alkaline earth metal of hydroxide or carbonate, organic base such as dicyclohexylamine or the like in a usual manner. The salt can be isolated by lyophylization or by filtration in a case when the product is enough insoluble in the reaction solvent, if necessary, after a portion of the solvent is removed.

Compound II can be also prepared as follows.

Route 2

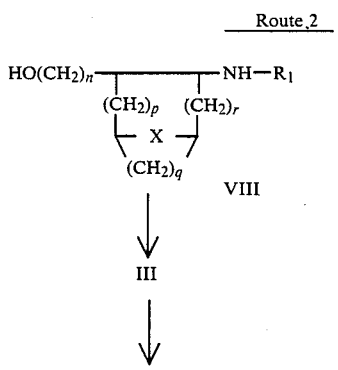

-continued
Route 2

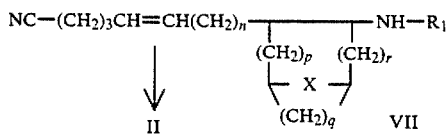
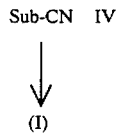

wherein $R_1$ is amino protecting group; n, p, q, X, and r each is the same as defined before.

1. Oxidation of the alcohol VIII to the aldehyde III.

The reaction is carried out using the following oxidizing agent: (1) a chromic acid-derived oxidizing agent, e.g., Collins' reagent, pyridinium chlorochromate or pyridinium dichromate; (2) dimethyl sulfoxide combined with oxalyl chloride, sulfuryl chloride or the like; or (3) pyridinium sulfur trioxide combined with a base such as triethylamine, 4-dimethylaminopyridine.

The reaction is achieved in a solvent, e.g., such as aromatic hydrocarbon, e.g., benzene, chlorinated hydrocarbon, e.g., chloroform, dichloromethane, ether, e.g., ethyl ether, ketone, e.g., acetone, or the like, which may be chosen according to the property of the agent used under cooling or warming within a period to several ten minutes to several hours.

2. Conversion of the aldehyde III into the compound VII by Wittig reaction.

The reaction is carried out using (4-cyanobutyl)triphenylphosphonium bromide as a Wittig agent in the same manner as in Step 1.

3. Conversion of the nitrile VII into the tetrazole II.

This step can be carried out according to a method of A. Nohara et al [J. Med. Chem., 22, 290, (1979)], W. G. Finnegan et al. [J. Am. Chem. Soc., 80, 3908, (1958)], or E. P. Vacek et al. Synthesis, 1133, (1987)]. The reaction can be carried out using azide salt such as ammonium azide, sodium azide, lithium azide, aluminium azide, trimethylsilyl azide, or the like in a solvent such as 1-methyl-2-pyrrolidinone, dimethylformamide, or dimethyl sulfoxide, ether (e.g., ethyl ether, tetrahydrofuran), or the like, with a catalyst such as triethylammonium chloride, ammonium chloride, tetramethylammonium chloride, or the like under heating for several hours.

The tetrazole derivatives prepared in this reaction can be converted into salts of tetrazole derivative by treating in the same manner as in Step 2.

The compounds of the present invention can be prepared as an alternative method by using a starting material which has a carboxyl group in place of tetrazolyl group of the compound.

Route 3

Sub-COOH(or its sodium salt)  VI

↓

Sub-CO-Hal  VI'

↓

Sub-CONH$_2$  V

↓

-continued
Route 3

Sub-CN  IV

↓

(I)

wherein Sub is

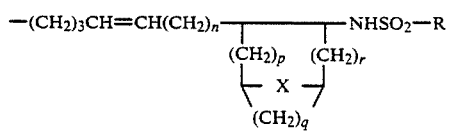

wherein R, X, n, p, q, and r, each has the same meaning as defined before; Hal is halogen.

1. The carboxylic acid VI is converted into the amide V.

This step can be carried out by treating an acid halide of the carboxylic acid VI with an aqueous ammonia.

The acid halide can be prepared using a halogenating agent such as thionyl chloride, phosgene, phophorous trichloride, phophorous pentachloride, or the like in aprotic solvent such as an aromatic hydrocarbon (e.g., benzene) under heating for several hours.

A treatment of the acid halide with ammonia is carried out in an ether (e.g., dioxane, tetrahydrofuran), water-soluble solvent (e.g., acetone), or the like at room temperature.

2. A carbamoyl of the compound V prepared above is dehydrated to converted into cyan to give the nitrile IV.

As a dehydrating agent, sulfuric acid, phosphorous pentoxide, phosphoryl chloride, polyphosphoric acid, trifluoroacetic acid, trifluoroacetic anhydride, or the like is exemplified.

The reaction can be carried out under anhydrous conditions in a solvent such as ether ( e.g., tetrahydrofuran, dioxane), chlorinated hydrocarbon ( e.g., dichloromethane, chloroform) under ice-cooling or at room temperature for several hours. If necessary, pyridine may be added.

3. The cyano of the compound IV is converted into tetrazolyl to give the compound I of the present invention.

This step can be carried out by the same procedure as in the third step of Route 2.

Compound IV can be also prepared from the compound VII which are prepared by the second step in Route 2, that is, after removal of the amino protecting group of the compound VII according to the method of Route 1, Step 2, the resulting product is treated by the method of Route 1, Step 3 to give the compound IV having the desired phenylsulfonlyamino.

Effects of the Invention

The objective compounds of the present invention strongly inhibit thromboxane $A_2$ related platelet aggregation, vasoconstriction, and bronchoconstriction. Therefore, clinical application of the compound can be expected, that is, the compounds can be used for treatment or improvement of such symptoms as arteriosclerosis, myocardial infarction, acute ischemic angina pectoris, cerebral infarction, circulatory shock, sudden death and so forth.

The objective compounds of the present invention can be administered orally or parenterally. For oral administration, the objective compound of the present invention can be used as conventional preparations, for example, solid preparation such as tablet, powder, capsule, or granule, or liquid preparation such as aqueous or oily suspension, syrup, or elixir. For parenteral administration, the objective compound of the present invention can be used as aqueous or oily suspension for injection. On its preparation, all of the commonly used vehicle, binder, lubricant, aqueous solvent, oily solvent, emulsifier, suspending agent, or the like can be used and other additives such as preservative, stabilizer, or the like may be contained therein.

The compound of the invention can be administered parenterally to an adult in an effective amount within the dosage range of about 0.001 mg to about 5 mg/Kg daily and especially about 0.005 mg/Kg to about 1 mg/Kg daily and orally within the dosage range about 0.01 mg/Kg to about 50 mg/Kg daily and especially about 0.05 mg/Kg to 10 mg/Kg daily on a regimen in a dose single or 2 to 5 divided doses; the dosage may be determined depending on administration route, patient's age, body-weight, and condition, and kind of disease.

The following examples are included to explain the embodiment of the present invention in more detail, but these are not intended to limit the scope of the invention.

In the following example, each compound is represented by one enantiomer. The relative configurations of racemates and the absolute configurations of optically active compounds are shown by R, S-designation of the compound name.

(1) (1R*,2S*,3S*,4S*)-3-Benzyloxycarbonylamino-2-formylmethylbicyclo [2.2.1]heptane 3a
(2) (1R*,2S*,3S*,4S*)-3-Benzyloxycarbonylamino-2-[6-(5-tetrazolyl) hex-2-enyl]bicyclo[2.2.1]heptane 2a
(3) (1R*,2S*,3S*,4S*)-3-Amino-2-[6-(5-tetrazolyl)hex-2-enyl]bicyclo[2.2.1]heptane, Trifluoroacetic acid salt 2a'
(4) (1R*,2S*,3S*,4S*)-2-[(2Z)-6-(5-Tetrazolyl)hex-2-enyl]-3-(4-tolylsulfonylamino) bicyclo[2.2.1]heptane Iab-a
(5) Sodium salt of (1R*,2S*,3S*,4S*)-2-[(2Z)-6-(5-tetrazolyl) hex-2-enyl]-3-(4-tolylsulfonylamino)bicyclo[2.2.1]-hepatane Iab-b (i) To 200 ml of dry dimethylsulfoxide is added 6 g (5.4×27.84 mM) of sodium hydride (60% suspension in mineral oil) and the mixture is stirred at 75° C. for 1.5 hours under nitrogen atmosphere. After the above mixture is cooled to room temperature, is added 39 g (3×27.84 mM) of triphenyl[4-(5-tetrazolyl) butyl]phosphonium bromide which is prepared by the method of Thomas K. Schaaf et al. [J. Med. Chem., 22, 1340, (1979)].

To the mixture stirred for 10 minutes is added a solution of 8.0 g (27.84 mM) of aldehyde 3a in 40 ml of dry dimethyl sulfoxide and the resulting mixture is stirred for 1 hour. The reaction mixture is added to a mixture of ice and ethyl acetate and adjusted to pH 2 with 2N hydrochloric acid. The organic layer is washed with water and concentrated under reduced pressure to give a residue as an oil, which is dissolved in toluene and extracted with a cold 1N sodium hydroxide. The aque-

EXAMPLE 1

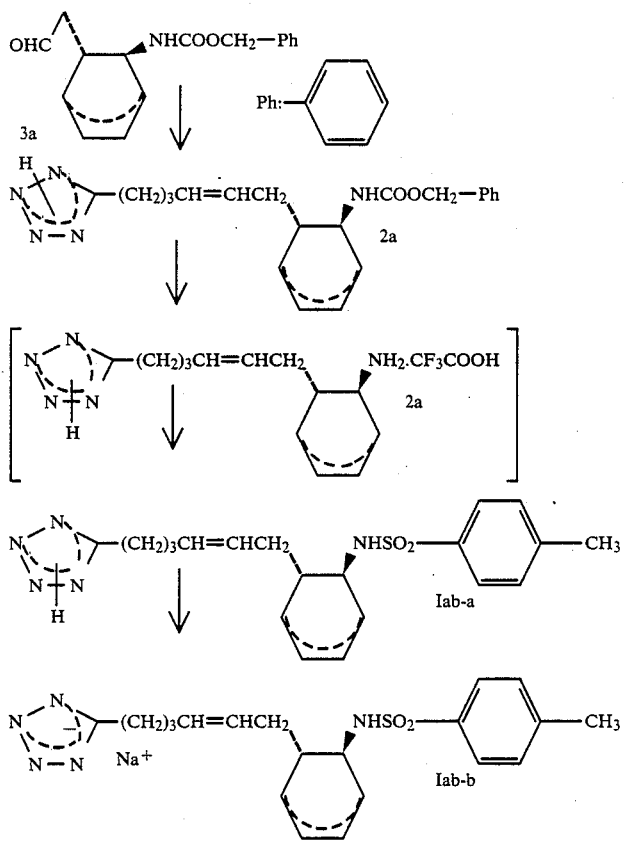

ous layer is acidified with 2N hydrochloric acid and extracted with ethyl acetate. After separation, the organic layer is washed with water, dried over magnesium sulfate, and concentrated under reduced pressure. The residue is chromatographed on silica gel and collected a fraction eluted with an n-hexane-ethyl acetate-dichloromethane (4:4:1) mixture to give 7.0 g of the desired compound 2a as a gum in 63.6% yield.

Anal. Calcd. (%) for $C_{22}H_{29}N_5O_2 \cdot 0.5CH_3COOC_2H_5$: C:65.57, H:7.57, N:15.95, Found (%): C:65.18, H:7.16, N:15.82.

IR$\nu$max(CHCl$_3$)cm$^{-1}$: 3445, 3145, 1697.

NMR δ ppm(CDCl$_3$): 0.90~2.08(m,14H), 2.35~2.48(m,1H), 2.80~3.03 (m,2H), 3.23~3.42(m,1H), 5.13(s,2H), 5.18~5.40(m,3H), 7.35(s,5H).

(ii) A mixture of 2.7 g of tetrazole 2a, 45 ml of trifluoroacetic acid, and 10 ml of anisole is heated at 45° C. for 7 hours. The reaction mixture is concentrated under reduced pressure and the resulting residue is rinsed with n-hexane to give 3.37 g of oily residue 2a' (theoretical weight 2.56 g, purity 76%).

(iii) To a solution of 680 mg (theoretical weight 516 mg, 1.38 mM) of the above crude product 2a' in 3 ml of dichloromethane and 2 ml of dimethylformamide are added 0.96 ml (5×1.38 mM) of triethylamine and then 526 mg (2×1.38 mM) of p-toluenesulfonyl chloride in a nitrogen atmosphere with ice cooling. The mixture is stirred for 20 minutes at the same temperature and poured into water. The mixture is extracted with ethyl acetate and the organic layer is washed with 2N hydrochloric acid and water, dried over magensium sulfate, and concentrated under reduced pressure to give a residue as an oil. To a solution of the resulting oil in 5 ml of methanol is added 2.76 ml (2×1.38 mM) of 1N sodium hydroxide and the mixture is stirred at room temperature for 10 minutes. The reaction mixture is poured into water, acidifed with 2N hydrochloric acid and extracted with ethyl acetate. After separation, the organic layer is washed with water, dried over magnesium sulfate, and concentrated under reduced pressure. The residue is chromatographed on silica gel and a fraction eluted with ethyl acetate-methanol (50:1) is collected to give 423 mg of desired compound Iab-a as a foam in 73.8% yield.

Anal. Calcd. (%) for $C_{21}H_{29}N_5O_2S \cdot 0.3CH_3COOC_2H_5$: C 60.32, H 7.16, N 15.85, S 7.26, Found (%) : C 60.60, H 7.19, N 15.91, S 6.98.

IR$\nu$max(CHCl$_3$)cm$^{-1}$: 3385, 3260, 1601, 1552, 1155, 1094.

NMR δ ppm(CDCl$_3$): 0.90~2.17(m,15H), 2.40(s,3H), 2.90~3.20(m, 3H), 5.06~5.43(m,2H), 5.83(d,J=6 Hz,1H), 7.24~7.35(m,2H), 7.73~7.85(m,2H), 13.10(br,1H), (iv) To a solution of 169 mg (0.4 mM) of tetrazolyl compound Iab-a in 2 ml of methanol is added 2.23 ml (0.182M solution in methanol; 0.4 mM) of sodium methoxide and the mixture is concentrated under reduced pressure. A solution of the resulting residue in 3 ml of water is lyophilized to give 157 mg of compound Iab-b as a colorless powder in 89.7% yield.

NMR δ ppm(d-methanol): 1.03~2.23(m,15H), 2.38(s,3H), 2.70~2.97(m,3H), 5.10~5.28(m,2H), 7.27~7.37(m,2H), 7.67~7.80 (m,2H).

EXAMPLES 2 TO 6

(1)(1R*,2S*,3S*,4S*)-3-(4-bromophenylsulfonylamino-2-[(2Z)-6-(5-tetrazolyl) hex-2-enyl]bicyclo[2.2.1]heptane Iac-a (2) (1R*,2S*,3S*,4S*)-3-(4-hydroxyphenylsulfonylamino)-2-[(2Z)-6-(5-tetrazolyl) hex-2-enyl]bicyclo[2.2.1]heptane Iad-a (3)(1R*,2S*,3S*,4S*)-3-(4-methoxyphenylsulfonylamino)-2-[(2Z)-6-(5-tetrazolyl) hex-2-enyl]bicyclo[2.2.1]heptane Iae-a (4) (1R*,2S*,3S*,4S*)-3-phenylsulfonylamino-2-[(2Z)-6-(5-tetrazolyl) hex-2-enyl]bicyclo[2.2.1]heptane Iaa-a (5) (1R,2S,3S,4S)-3-phenylsulfonylamino-2-[(2Z)-6-(5-tetrazolyl) hex-2-enyl]bicyclo[2.2.1]heptane (+)-Iaa-a (i) The compounds shown in Table 1 are prepared by the same procedure as that of Example 1-(iii) using 4-bromophenylsulfonyl chloride, 4-acetoxyphenylsulfonyl chloride, 4-methoxy phenylsulfonyl chloride, or phenylsulfonyl chloride instead of p-toluenesulfonyl chloride.

(ii) The compounds shown in Table 2 are prepared by treating the compounds shown in Table 1 with the same manner as that of Example 1-(iv).

TABLE 1

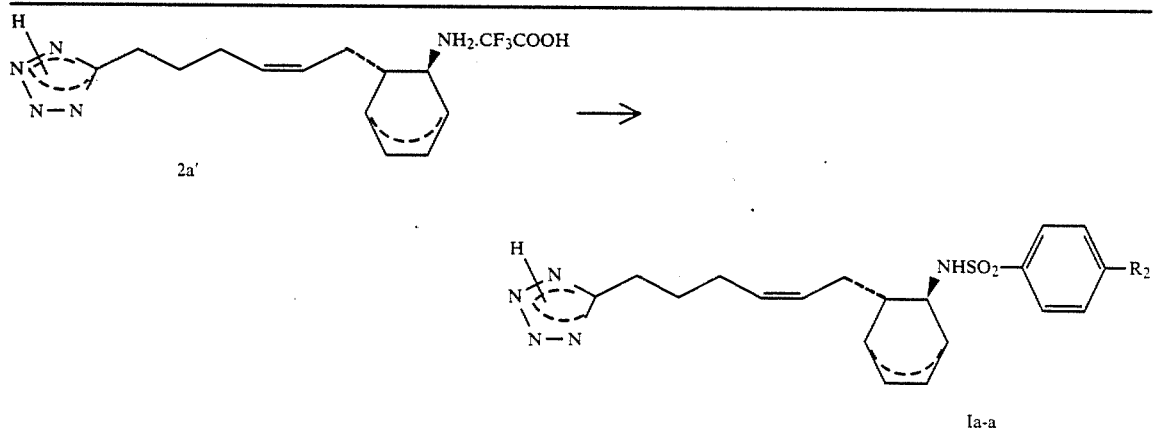

| Example Number | Compd. Number | R$_2$ | IR ν max (cm$^{-1}$) | NMR δ ppm | Analysis (Molecular formula) Calcd. (%) Found (%) |
|---|---|---|---|---|---|
| 2-(i) | I ac-a | Br | (CHCl$_3$) 3385, 3265, 1578, 1152, | (d-Methanol) 0.95~2.16(m,15H), 2.83~2.98 (m,3H), 2.05~2.40 | (C$_{20}$H$_{26}$BrN$_6$O$_2$S·0.3CH$_3$COOC$_2$H$_5$) · C:50.23 H:5.65 N:13.82 S:6.33 Br:15.76 |

4,916,231

TABLE 1-continued

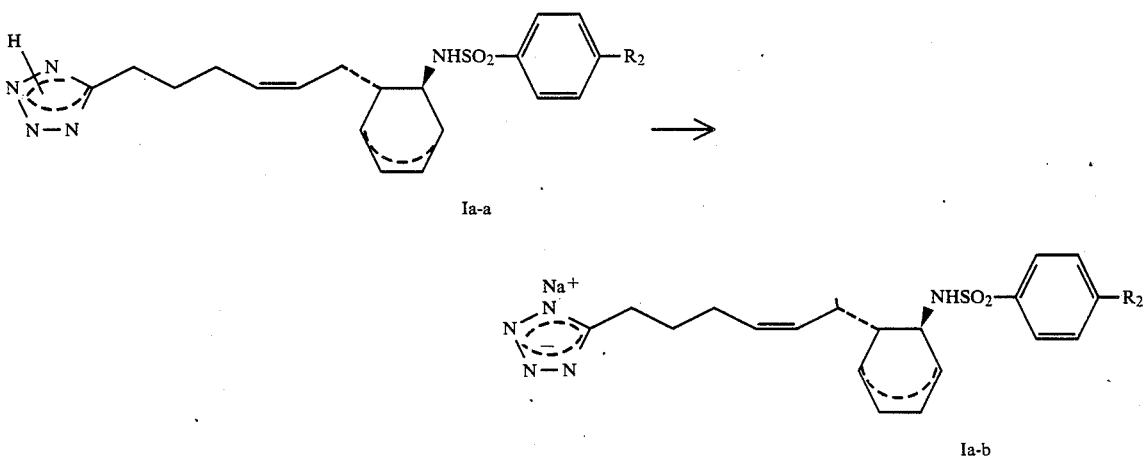

| Example Number | Compd. Number | $R_2$ | IR ν max (cm$^{-1}$) | NMR δ ppm | Analysis (Molecular formula) Calcd. (%) Found (%) |
|---|---|---|---|---|---|
| 3-(i) | I ad-a | OH | 1092, 1070. (KBr) 3280br, 1645, 1605, 1588, 1150, 1093. | (d-Methanol) 0.92~2.16(m,15H) 2.77~2.99 (m,3H), 5.05~5.73 (m,2H), 6.30~6.93 (m,2H), 7.57~7.75 (m,2H) (m,2H), 7.64~7.85 (m,4H) | C:49.93 H:5.58 N:13.64 S:6.17 Br:15.49 ($C_{20}H_{27}N_5O_3S \cdot CH_3COOC_2H_5$) C:57.00 H:6.98 N:13.85 S:6.34 C:56.88 H:6.64 N:13.54 S:6.16 |
| 4-(i) | I ae-a | OCH$_3$ | (CHCl$_3$) 3385, 3245, 1645br, 1600, 1581, 1150, 1096. | (CDCl$_3$) 0.85~2.10 (m,15H), 2.92~3.07 (m,3H), 3.84 (s,3H), 5.08~5.42 (m,2H), 5.60~5.85 (m,1H), 6.85~7.00 (m,2H), 7.75~7.88 (m,2H), 11.13 (br 1H) | ($C_{21}H_{29}N_5O_3S \cdot 0.6CH_3COOC_2H_5 \cdot 0.8H_2O$) C:56.33 H:7.15 N:14.04 S:6.43 C:55.88 H:6.55 N:14.51 S:6.39 |
| 5-(i) | I aa-a | H | (CHCl$_3$) 3385, 3260, 1603, 1553, 1156, 1094. | (CDCl$_3$) 0.90~2.11 (m,15H), 2.95~3.10 (m,3H), 5.21~5.32 (m,2H), 5.67 (d,J=7Hz,1H), 7.48~7.57 (m,3H), 7.86~7.95 (m,2H). | ($C_{20}H_{27}N_5O_2S \cdot 0.1CH_3COOC_2H_5$) C:59.70 H:6.63 N:17.07 S:7.81 C:59.30 H:6.87 N:16.67 S:7.52 |
| 6-(i) | (+)Iaa-a | H | (CHCl$_3$) 3390, 3275, 1603, 1551, 1155, 1094. | Identical with compound Iaa-a. | $C_{20}H_{27}N_5O_2S \cdot 0.13C_6H_6$ C:60.62 H:6.80 N:17.01 S:7.79 C:60.20 H:6.78 N:16.50 S:7.41 |

TABLE 2

| Example Number | Compd. Number | $R_2$ | IR ν max (cm$^{-1}$) | NMR δ ppm | Analysis (Molecular formula) Calcd. (%) Found (%) |
|---|---|---|---|---|---|
| 2-(i) | I ac-b | Br | (KBr) 3420br, 3280, 1698br, 1637br, 1576, 1165, 1092, 1068. | (d-Methanol) 1.00~2.20(m,15H), 2.70~2.97 (m,3H), 5.06~5.27 (m,2H), 7.61~7.83 (m,4H) | ($C_{20}H_{25}N_5BrO_2SNa \cdot 1.5H_2O$) C:45.36 H:5.33 N:13.22 S:6.06 C:45.79 H:5.28 N:12.79 S:5.94 |
| 3-(i) | I ad-b | OH | (KBr) | (d-Methanol) 1.00~2.15(m,15H), 2.71~2.98 (m,3H), 5.17~5.42 (m,2H), 6.60~6.78 (m,2H), 7.42~7.63 (m,2H) | |
| 4-(i) | I ae-b | OCH$_3$ | (KBr) | (d-Methanol) 0.95~2.20(m,15H), 2.70~2.93 (m,3H), 3.82 (s,3H), 5.06~5.35 (m,2H), 6.95~7.07 | |

TABLE 2-continued

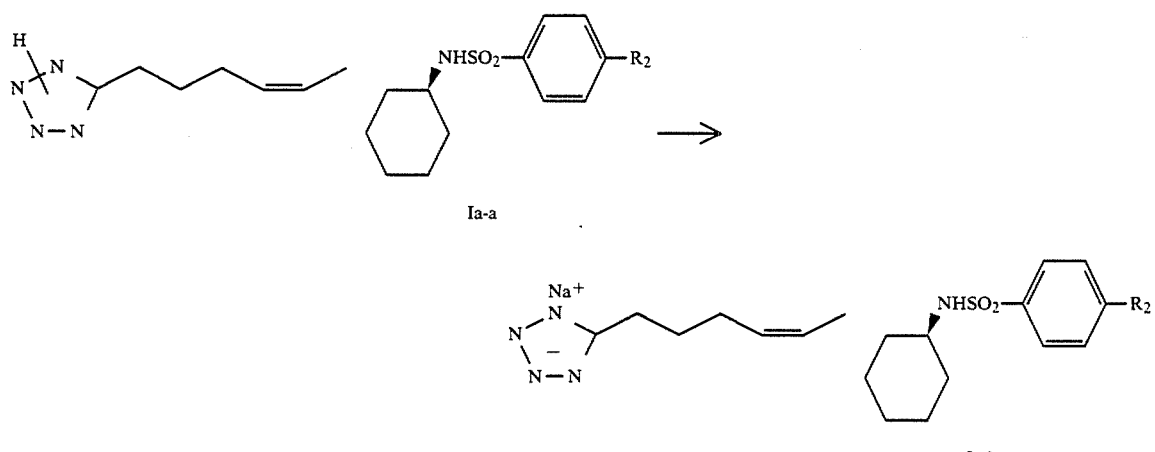

| Example Number | Compd. Number | R₂ | IR ν max (cm⁻¹) | NMR δ ppm | Analysis (Molecular formula) Calcd. (%) Found (%) |
|---|---|---|---|---|---|
| 5-(i) | I aa-b | H | (Nujol) 3540, 3265, 1577, 1156, 1094, 754, 720, 685, 590, 557. | (m,2H), 7.70~7.84 (m,2H) (d-Methanol) 1.03~2.18(m,15H), 2.77 (t,J=6Hz,2H), 2.80~2.97 (m,1H), 4.97~5.40(m,2H), 7.48~7.60 (m,3H), 7.82~7.92 (m,2H). | ($C_{20}H_{26}N_5O_2SNa \cdot 1H_2O$) C:54.40 H:6.39 N:15.86 S:7.26. C:54.12 H:6.30 N:15.66 S:6.91 |
| 6-(i) | (+)Iaa-b | H | (KBr) 3490, 3280, 1637, 1584, 1448, 1320, 1158, 1096, 590. | Identical with compound Iaa-b. $[\alpha]_D$ +42.8 ± 0.7 (24° C., c 1.238, H₂O) | ($C_{20}H_{26}N_5O_2SNa \cdot 1H_2O$) C:54.40 H:6.39 N:15.86 S:7.26 C:54.23 H:6.19 N:15.73 S:7.28 |

Preparation of Intermediate 1

(1) Preparation of (1S,2R,3S,4R)-bicyclo[2.2.1]hept-5-en-2, 3-dicarboxylic acid 2-(benzyl D-mandelate) ester 2

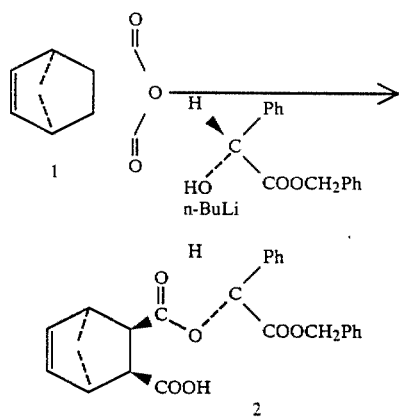

In a nitrogen atmosphere, a solution 5.33 g (22.0 mmol) of benzyl D-mandelate in 50 ml of tetrahydrofuran (THF) is cooled to −78° C., then 13.13 ml (21.0 mmol) of 1.6M solution of n-butyllithium in hexane is added dropwise and the mixture is stirred for 15 minutes. To the reaction mixture is added a solution of 3.32 g (20.0 mmol) of bicyclo[2.2.1]hept-5-en-2-endo, 3-endo-dicarboxylic acid 1 in 20 ml of THF and the resulting mixture is stirred for an hour at −78° C. The reaction mixture is acidified with 2N hydrochloric acid and the product is extracted with ethyl acetate. The organic layer is washed with water and an aqueous solution of sodium chloride and concentrated to give 9.33 g of the crude product 2 which is purified by column chromatography on silica gel (toluene-ethyl acetate).

IR(film)νmax: 3600–2400, 1748, 1710, 1498, 1456, 1342, 1257, 1208, 1165, 1084, 1072, 912, 732, 696 cm⁻¹.

(2) Preparation of (1R,2R,3S,4S)-bicyclo[2.2.1]heptan-2,3-dicarboxylic acid 2-(D-mandelic acid) ester 3a

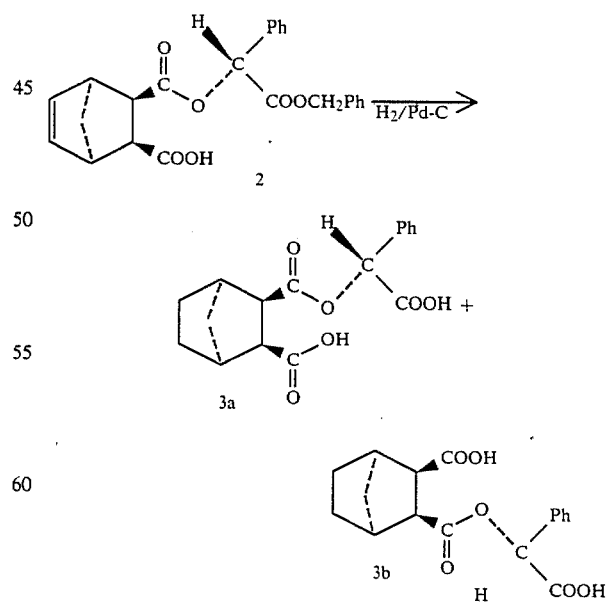

To a solution of 4.06 g (10.0 mmol) of crude product 2 in 30 ml of methanol is added 0.4 g of 10% palladium-carbon and the mixture is stirred in a hydrogen atmosphere under ordinary pressure at room temperature for 1.5 hours. The reaction mixture is filtered to remove the catalyst and the filtrate is concentrated. The residue is partitioned between ethyl acetate and 5% aqueous solution of sodium hydrogencarbonate and the aqueous layer is separated. The organic layer is extracted with water. The aqueous layers are collected and washed with ethyl acetate. After acidification with 2N hydrochloric acid the mixture is extracted with ethyl acetate. The organic layer is washed with an aqueous solution of sodium chloride and concentrated to give 3.14 g of the crude product 3a in 99% yield from acid anhydried. Compound 3a: Compound 3b=86:14 (Determined by HPLC).

The desired compound 3a is isolated by recrystallization from ethyl acetate. (2.05 g, yield 64%).

Mp. 164°–166° C.

$[\alpha]_D = -117.1 \pm 0.8°$ (MeOH, c=1.934, 25° C.).

(3) Preparation of (1R,2S,3S,4S)-2-carbomethoxy-3-carboxybicyclo [2.2.1]heptane 4.

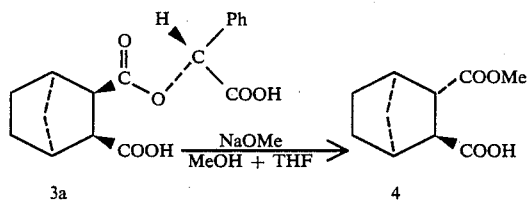

In a nitrogen atmosphere, a mixture of 5.51 g (17.3 mmol) of compound 3a, 40 ml of THF, 50 ml of methanol, and 22.0 ml (44.0 mmol) of sodium methylate (2M solution in methanol) is refluxed for 4 hours. To the reaction mixture is added 2N hydrochloric acid and the mixture is extracted with ethyl acetate. The organic layer is washed with water and a saturated aqueous solution of sodium chloride, and concentrated. The residue is dissolved in dichloromethane and washed three times with water. The organic layer is concentrated to give 3.22 g of the desired compound 4 in 94% yield.

Mp. 59°–60° C.

$[\alpha]_D = +38.4 \pm 0.4°$ (MeOH, c=2.002, 25° C.).

(4) Preparation of (1R,2S,3S,4S)-methyl 3-benzyloxycarboxylaminobicyclo [2.2.1]heptan-2-carboxylate 5

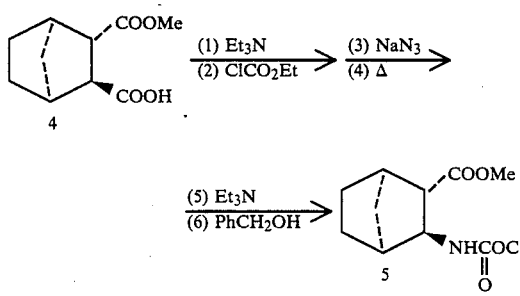

In a nitrogen atmosphere, a solution of 2.80 g (14.1 mmol) of the compound 4 in 24 ml of acetone is cooled to 0° C. and 2.54 ml (18.3 mmol) of triethylamine and 1.75 ml (18.3 mmol) of ethyl chlorocarbonate are added thereto. Then, colorless solids are precipitated immediately. The mixture is stirred for 15 minutes and a solution of 2.75 g (42.3 mmol) of sodium azide in 8 ml of water is added. The mixture is stirred under ice-cooling and acidified with 2N hydrochloric acid. The resulting mixture is extracted with ethyl acetate and the organic layer is washed with water and then with an aqueous solution of sodium chloride and concentrated. Benzene is added to the residue and concentrated again in order to removed ethyl acetate completely.

The resulting oil is dissolved in 20 ml of benzene and the mixture is heated to 80° C. to perform thermal rearrangement. When the evalution of nitrogen gas has ceased, 2.54 ml (18.3 mmol) of triethylamine and 1.75 ml (16.9 mmol) of benzyl alcohol are added and the resulting mixture is refluxed for 1.5 hours. After the reaction is finished, 2N hydrochloric acid is added to the reaction mixture which is then extracted with ethyl acetate. The organic layer is washed with water, and then with aqueous solution of sodium chloride and concentrated. The crude product is purified by column chromatography on silica gel and recrystallized to give 3.03 g of the compound 5 in 71% yield.

Mp.: 61°–62° C.

$[\alpha]_D = +40.1 \pm 0.4°$ (CHCl$_3$, c=2.006, 25° C.).

(5) Preparation of (1R,2S,3S,4S)-3-benzyloxycarbonylaminobicyclo [2.2.1]heptan-2-carboxylic acid 6

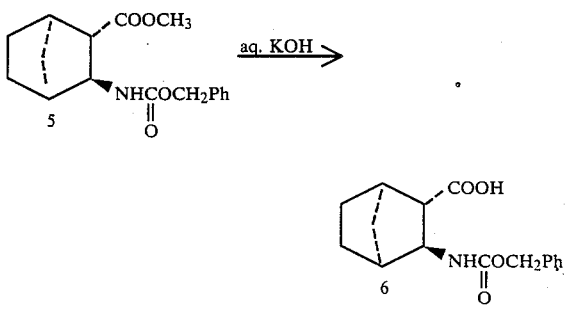

To a solution of 15.25 g (50.3 mmol) of the starting material 5 in 200 ml of methanol is added 100 ml (2×50.3 mmol) of 1N potassium hydroxide in a nitrogen atmosphere and the mixture is stirred for 2.5 hours at room temperature. The reaction mixture is poured into water and then acidified with 2N hydrochloric acid in the presence of ethyl acetate. The organic layer is washed with a saturated aqueous solution of sodium chloride, dried over magnesium sulfate, and concentrated under reduced pressure. The residue is recrystallized from n-hexane-ethyl acetate to give 14.10 g of the desired compound 6 in 96.9% yield.

Mp. 104.5°–106.5° C.

Anal. Calcd. (%) for C$_{16}$H$_{19}$NO$_4$=289.33: C, 66.42; H, 6.62; N, 4.84; Found (%): C, 66.48; H, 6.61; N, 4.80.

$[\alpha]_D = +20.8 \pm 0.6°$ (c=1.010, CHCl$_3$, 23° C.).

IR(CHCl$_3$)$\nu$max: 3440, 2960, 2880, 2720, 1745, 1705, 1670, 1515 cm$^{-1}$.

NMR(CDCl$_3$) δ ppm: 1.17~1.82(m.6H), 2.15(br.s, 1H), 2.43(br.s, 1H), 2.75~2.85(m, 1H), 3.83~3.93(m, 1H), 5.13(ABq, Apart, J=11.8, 1H), 5.18(ABq, Bpart, J=12.0 Hz, 1H), 5.29(br.s, 1H), 7.38(br.s, 5H).

(6) (1R,2S,3S,4S)-3-benzyloxycarbonylaminobicyclo[2.2.1]heptan-2-carbaldehyde 7

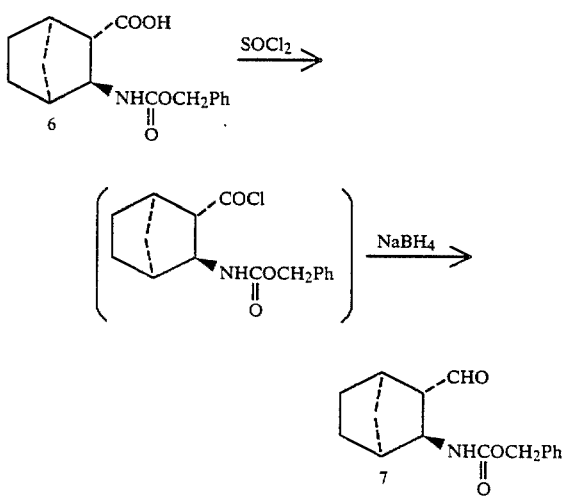

To a solution of 6.0 g (20.74 mmol) of carboxylic acid 6 in 100 ml of dry benzene are added 7.48 ml (5×20.74 mmol) of thionyl chloride and then 300 μl of pyridine and the mixture is heated under refluxing for an hour. The reaction mixture is concentrated under reduced pressure and 30 ml of dry benzene is added thereto and the resulting mixture is concentrated under reduced pressure again to give the intermediate, acid chloride, quantitatively.

IR(film)νmax: 3285, 1782, 1692, 1515, 1261 cm$^{-1}$.

In a nitrogen atmosphere, 628 mg (0.8×20.74 mmol) of sodium borohydride is added to 36 ml of dry dimethylformamide and then 54 ml of dry tetrahydrofuran is added thereto to prepare a homogenious solution, which is cooled to −70° C. to give a solid. Two minutes later, the mixture is warmed to 0° C. and then 2 minutes later the resulting paste is cooled to −70° C. To the mixture is added to solution of 20.74 mmol of the above prepared acid chloride in 12 ml of dry tetrahydrofuran over a minute.

The resulting mixture is stirred vigorously for 2 minutes and 40 ml of ethyl vinyl ether is added thereto. The mixture is poured into a ice-cold mixture of 20 ml of 2N hydrochloric acid and 80 ml of n-propionic acid under stirring vigorously. Further, 200 ml of saturated aqueous solution of sodium chloride and 100 ml of ethyl acetate are added and the resulting mixture is stirred for 2 minutes. The organic layer is separated and washed with a saturated aqueous solution of sodium chloride, 1N sodium hydroxide, and a saturated aqueous solution of sodium chloride again, successively, dried over magnesium sulfate, and concentrated under reduced pressure to give 4.23 g of the desired aldehyde 7 as an oil in 74.6% yield from the compound 6.

NMR(CDCl$_3$)δ ppm: 1.10~1.80(m, 6H), 1.88~2.05(m, 1H), 2.40~2.60(m, 2H), 4.15~4.26(m, 1H), 4.80~5.16(m, 1H), 5.10(s,2H), 7.36(s, 5H), 9.78(s, 1H).

(7) Preparation of (1R,2R,3S,4S)-(5Z)-methyl 6-(3-benzyloxycarbonylaminobicyclo[2.2.1]hept-2-yl)-5-hexenoate 8a

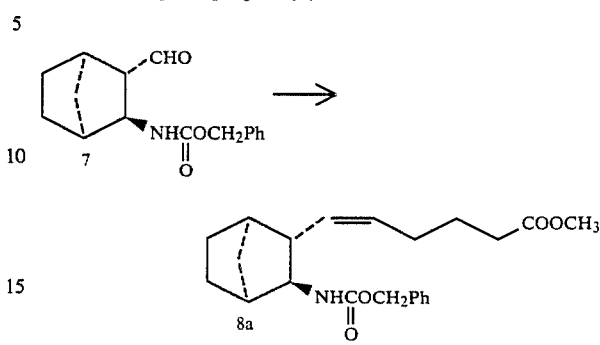

To a stirring suspension of 9.5 g (3×7.13 mmol) of 4-carboxybutyltriphenylphosphonium bromide in 90 ml of tetrahydrofuran under a nitrogen atmosphere, 4.3 g (5.4×7.13 mmol) of potassium tert-butoxide is added thereto, and the mixture is stirred for 30 minutes at room temperature. To the above mixture is added a solution of 1.95 g (7.13 mmol) of the aldehyde 7 in 10 ml of dry tetrahydrofuran and the mixture is stirred at room temperature for an hour. The reaction mixture is poured into a mixture of 2N hydrohloric acid and ethyl acetate. After separation, the organic layer is washed with water, dry over magnesium sulfate, and concentrated under reduced pressure to give an oily residue, which is methylated with diazomethane in ethyl ether. The solvent is evaporated and the residue is chromatographed on silica gel. The fractions eluted with n-hexane-ethyl acetate (4:1) are collected to give 946 mg of the desired compound 8a as an oil in 35 .7% yield.

IR(CHCl$_3$)νmax: 3460, 1726, 1510, 1015 cm$^{-1}$.

NMR(CDCl$_3$) δ ppm: 1.16~1.75(m, 8H), 1.79~1.95(m, 2H), 2.03(q, J=7 Hz, 2H), 2.28(t, J=7 Hz, 2H), 2.47(br.s, 1H), 3.64(br.s, 4H), 4.97~5.18(m, 1H), 5.05(ABqApartJ=12 Hz, 1H), 5.11(ABqBpartJ=12 Hz, 1H), 5.23~5.45(m, 2H), 7.35(s, 5H).

(8) Preparation of (1R,2R,3S,4S)-3-benzyloxycarbonylamino-2-[(1Z)-5-(5-tetrazolyl)-1-pentenyl]bicyclo[2.2.1]heptane 2b

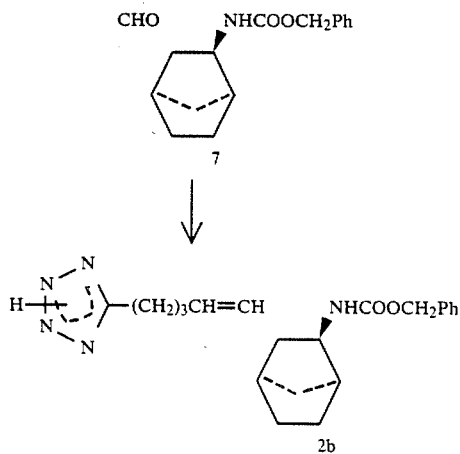

In a nitrogen atmosphere, to a suspension of 11.7 g (3×8.3 mmol) of triphenyl [4-(5-tetrazolyl)butyl]phosphonium bromide in 110 ml of dry tetrahydrofuran is added 5.0 g (5.4×8.3 mmol) of potassium tert-butoxide and the mixture is stirred at room temperature for 0.5 hours. Under ice-cooling, a solution of 2.28 g (8.3 mmol) of the starting material 7 in 15 ml of dry tetrahydrofuran is added thereto and the mixture is stirred at the same temperature for an hour. The reaction mixture is poured into a mixture of 2N hydrochloric acid and ethyl acetate and separated. The organic layer is washed with water, dried over magnesium sulfate, and concentrated under reduced pressure to give an oily residue which is chromatographed on a silica gel column. The fractions eluted with toluene-ethyl acetate (2:1) mixture are collected to give 1.50 g of crystalline residue which is recrystallized from ethyl ether to give 1.01 g of desired compound 2b in 31.9% yield.

mp. 150°–153° C.

Anal. Calcd. (%) for $C_{21}H_{27}N_5O_2$: C, 66.11; H, 7.13; N, 18.36; Found (%): C, 65.94; H, 7.41; N, 18.14.

$[\alpha]_D$: −31.3±0.7° (c=0.992, MeOH 24° C.)

IR(CHCl$_3$)νmax: 3245, 3110, 1672, 1562, 1455, 1301, 1284 cm$^{-1}$.

NMR(CD$_3$OD)δ ppm: 1.10~1.90(m, 9H), 1.95~2.20(m, 3H), 2.87(t, J=7.9 Hz, 2H), 3.46~3.57(m, 1H), 5.01(s, 2H), 5.25~5.48(m, 2H), 7.20~7.44(m, 5H), 7.53~7.74(m, 1H).

EXAMPLE 7

Preparation of (1R,2R,3S,4S)-3-phenylsulfonylamino-2-[(1Z)-5-(5-tetrazolyl)-1-pentenyl]bicyclo[2.2.1]heptane Ifa-a and its sodium salt Ifa-b

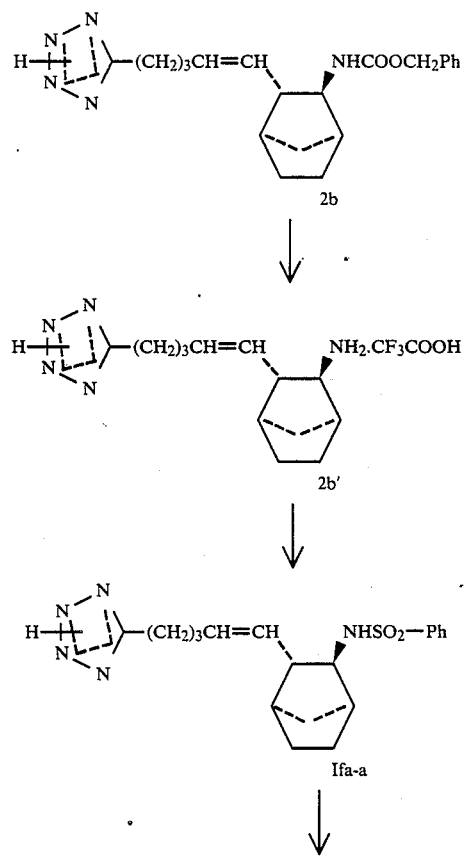

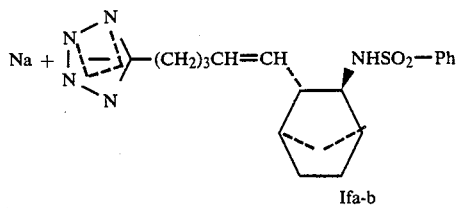

(i) A mixture of 1.03 g of tetrazole 2b in 5 ml of anisole and 20 ml of trifluoroacetic acid is heated at 45° C. for 7 hours. The solvent is evaporated under reduced pressure and the residue is rinsed with n-hexane under ice-cooling to give 1.416 g of gummy substance containing compound 2b' in 68.8% purity from the theory.

To a solution of 452 mg (1.25 mmol) of tetrazole 2b' in a mixture of 4 ml of dichloromethane and 1 ml of dimethylformamide are added 1.0 ml (6×1.25 mmol) of triethylamine and then 0.4 ml (2.5×1.25 mmol) of phenylsulfonyl chloride in a nitrogen atmosphere under ice-cooling and the mixture is stirred at the same temperature for an hour. The reaction mixture is poured into a mixture of 2N hydrochloric acid and ethyl acetate. The organic layer is separated, washed with water, and concentrated under reduced pressure. To a solution of the oily residue in 5 ml of methanol is added 2.5 ml of 1N sodium hydroxide and the mixture is allowed to stand at room temperature for an hour. The reaction mixture is partitioned between water and ethyl ether. The aqeuous layer is acidified with 2N hydrochloric acid in the presence of ethyl acetate. The organic layer is separated, washed with a saturated aqueous solution of sodium chloride, dried over magnesium sulfate, and concentrated under reduced pressure. The residue is chromatographed on silica gel and the fractions eluted with toluene- ethyl acetate (1:1) to ethyl acetate -methanol (10:1) are collected to give 129 mg of the desired compound Ifa-a as a gum in 26.6% yield.

IR(CHCl$_3$)νmax: 3210br, 1670br, 1550, 1155, 1095 cm$^{-1}$.

NMR(CDCl$_3$)δ ppm: 1.10~2.25(m, 13H), 2.94~3.16(m, 2H), 3.23~3.35 (m, 1H), 5.15~5.38(m, 2H), 5.69(d, J=7.5), 7.43~7.66(m, 3H), 7.80~7.94(m, 2H).

(ii) To a solution of 114 mg of the starting material Ifa-a in 2 ml of methanol is added 1.58 ml of 0.177N sodium methoxide under ice-cooling and two minutes later, the mixture is concentrated. The residue is dissolved in 2 ml of water to lyophilized and gives 115 mg of the desired Ifa-b as an powder in 97.5% yield.

$[\alpha]_D$ −51.7±1.3° (c=0.692 MeOH 23° C.).

IR(KBr)νmax: 3410br, 1640, 1603, 1448, 1320, 1310, 1160, 1094 cm$^{-1}$.

NMR(CD$_3$OD)δ ppm: 1.13~2.21(m, 13H), 2.73(t, J=7 Hz, 2H), 3.10~3.18(m, 1H), 4.98~5.19(m, 2H), 7.38~7.60(m, 3H), 7.75~7.88(m, 2H).

EXAMPLE 8

Preparation of (1R,2R,3S,4S)-3-(4-bromophenylsulfonylamino)-2-[(1Z)-5-(5-tetrazolyl) pent-1-enyl]bicyclo[2.2.1]heptane Ifc-a and its sodium salt Ifc-b

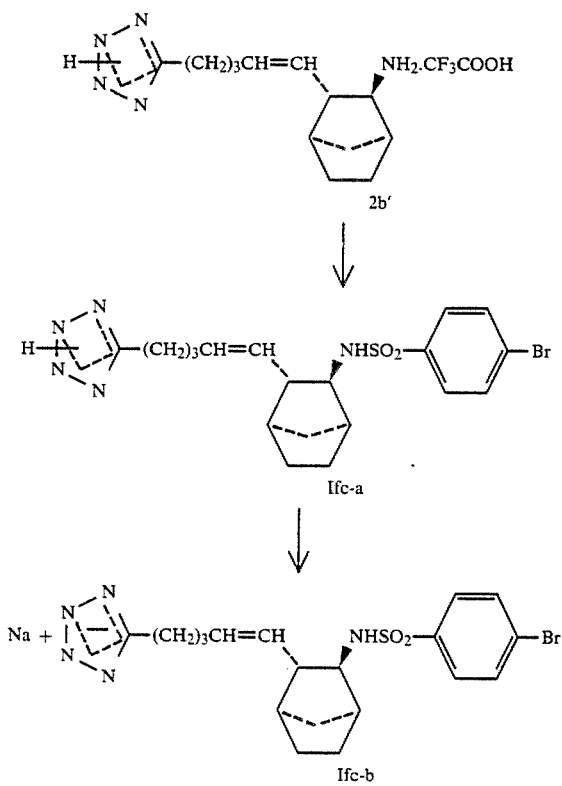

To a solution of 749 mg (1.43 mmol) of the starting material 2b' in a mixture of 4 ml of dichloromethane and 1 ml of dimethylformamide are added 1.19 ml(6×1.43 mmol) of triethylamine and 0.91 g (2.5×1.43 mmol) of 4-bromobenzenesulfonyl chloride in a nitrogen atmosphere under ice-cooling and the mixture is stirred at the same temperature for 1.5 hours. The reaction mixture is poured into a mixture of 2N hydrochloric acid and ethyl acetate. The separated organic layer is washed with a saturated aqueous solution of sodium chloride, dried over magnesium sulfate, and concentrated under reduced pressure to give the oily residue, which is dissolved in 6 ml of methanol. To the resulting solution is added 1N sodium hydroxide and the mixture is allowed to stand at room temperature for 15 minutes. The reaction mixture is poured into water and washed with ethyl ether. The aqueous layer is acidifed with 2N hydrochloric acid in the presence of ethyl acetate. After separation, the organic layer is washed with a saturated aqueous solution of sodium chloride, dried over magnesium sulfate, and concentrated under reduced pressure. The residue is chromatographed on a silica gel column and the fractions eluted with toluene-ethyl acetate (1:1) to ethyl acetate-methanol (10:1) are collected to give 330 mg of the aimed compound Ifc-b as a gummy residue in 49.5% yield.

Anal. Calcd. (%) for $C_{19}H_{24}N_5BrO_2S \cdot 0.32\ C_6H_6$: C, 51.13; H, 5.32; N, 14.25; S, 6.52; Found (%): C, 50.73; H, 5.41; N, 13.92; S, 6.03.

$[\alpha]_D = -66.6 \pm 1.1°$ (MeOH, c=1.016).

IR(KBr)$\nu$max: 3260(br), 2950, 2880, 1635, 1575, 1555, 1470, 1390, 1322, 1150, 1090, 1068, 1010 cm$^{-1}$.

NMR(CDCl$_3$)δ ppm: 1.10~2.23(m, 13H), 3.07(t, J=7.0 Hz, 2H), 3.28(br, s, 1H), 5.10~5.40(m, 3H), 6.12(br, s, 1H), 7.55~7.80(m, 4H).

(ii) Compound Ifc-a is treated with the same procedure as that of Example 7 to give its sodium salt Ifc-b.

Anal. Calcd. (%) for $C_{19}H_{23}N_5BrO_2SNa \cdot 1.5\ H_2O$: C, 44.28; H, 5.08; N, 13.59; S, 6.22; Found (%): C, 44.73; H, 5.08; N, 13.12: S, 6.64

$[\alpha]_D = -62.8 \pm 1.0°$ (MeOH, c=1.014).

IR(KBr)$\nu$max: 3400(br), 2950, 2870, 1640. (br), 1575, 1473, 1390, 1325, 1165, 1092, 1068, 1010 cm$^{-1}$.

NMR(CD$_3$OD)δ ppm: 1.10~2.04(m, 12H), 2.15(br, s, 1H), 2.73(t, J=7.3 Hz, 2H), 3.03~3.16(m, 1H), 4.93~5.20(m, 2H), 7.50~7.76(m, 4H).

General Procedure of Examples 9 to 12

EXAMPLE 9

Preparation of (1R*,2R*,3R*,4S*)-3-phenylsulfonylamino-2-[(2Z)-6-(5-tetrazolyl) hex-2-enyl]-7-oxabicyclo[2.2.1]heptane Iba-a and its sodium salt Iba-b

EXAMPLE 10

Preparation of (1R*,2S*,3S*,4S*)-3-phenylsulfonylamino-2-[(2Z)-6-(5-tetrazolyl) hex-2-enyl]-7-oxabicyclo[2.2.1]heptane Ica-a and its sodium salt Ica-b

EXAMPLE 11

Preparation of 1S,2S,3S,5R)-3-phenylsulfonylamino-2-[(2Z)-6-(5-tetrazolyl) hex-2-enyl]-6,6-dimethylbicyclo [3.1.1]heptane Ida-a and its sodium salt Ida-b

EXAMPLE 12

Preparation of (1R,2R,3S,5S)-2-phenylsulfonylamino-3-[(2Z)-6-(5-tetrazolyl) hex-2-enyl]-6,6-dimethylbicyclo[3.1.1]heptane Iea-a and its sodium salt Iea-b The starting materials which are the carboxylic acids or their sodium salts shown below are allowed to react under the condition shown in Table 3. The results are shown in Tables 4 to 7.

EXAMPLE 9

Sodium 5(Z)-7-[(1R*,2R*,3R*,4S*)-3-phenylsulfonylamino-7-oxabicyclo [2.2.1]hept-2-yl]-5-heptenoate 6b

EXAMPLE 10

5(Z)-7-[(1R*,2S*,3S*,4S*)-3-phenylsulfonylamino-7-oxabicyclo-[2.2.1]hept-2-yl]-5-heptenoic acid 6c

EXAMPLE 11

5(Z)-7-[(1S,2S,3S,5R)-3-phenylsulfonylamino-6,6-dimethyl-bicyclo [3.1.1]hept-2-yl]-5-heptenoic acid 6d

EXAMPLE 12

Sodium 5(Z)-7-[(1R,2R,3S,5S)-2-phenylsulfonylamino-6,6-dimethylbicyclo [3.1.1]hept-3-yl]-5-heptenoate 6e

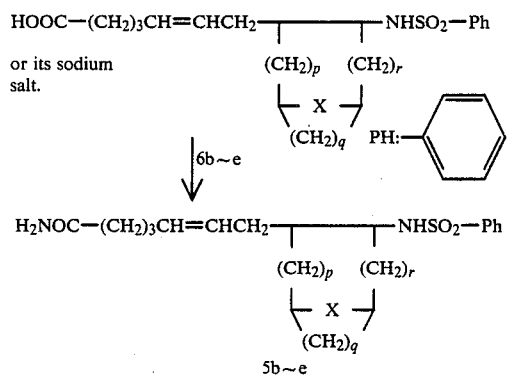

To a solution of [A] g of carboxylic acid (or its sodium salt) 6b-e in [B] ml of benzene is added [C] ml of thionyl chloride and the mixture is refluxed for two hours under heating. The reaction mixture is evaporated under reduced pressure. A solution of resulting residue in [D] ml of tetrahydrofuran is added to [E] ml of 28% aqueous ammonia and the mixture is stirred for 3 hours. The reaction mixture is extracted with ether and the extract is washed with water, dried over anhydrous sodium sulfate, and evaporated under reduced pressure. The resulting residue is purified by flash column chromatography ([F] g of silica gel, 230–400 mesh, hexane-ethyl acetate-methanol [G:H:I→J:K:L]) to give the purpose compound 5b-e.

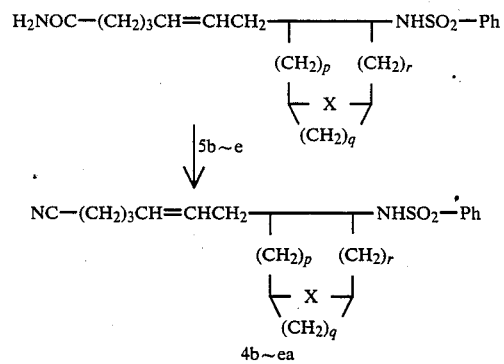

To a solution of [M] g of amide 5b-e prepared in (i) in [N] ml of dry dioxane is added [O] mg of pyridine and a solution of [P] mg of trifluoroacetic anhydride in 3 ml of dioxane is added thereto over 1 hour with stirring under ice cooling in a nitrogen atmosphere. The resulting mixture is stirred at room temperature for additional 3 hours and the reaction mixture is poured into a mixture of ice- ether. The ether layer is separated and washed with diluted hydrochloric acid, 5% sodium hydrogencarbonate, and water, successively, dried over anhydrous sodium sulfate, and evapoarted under reduced pressure. The residue is purified by flash chromatography ([Q] g of silica gel, 230–400 mesh, hexaneethyl acetate [R:S→T:U] to give a nitrile 4b-ea.

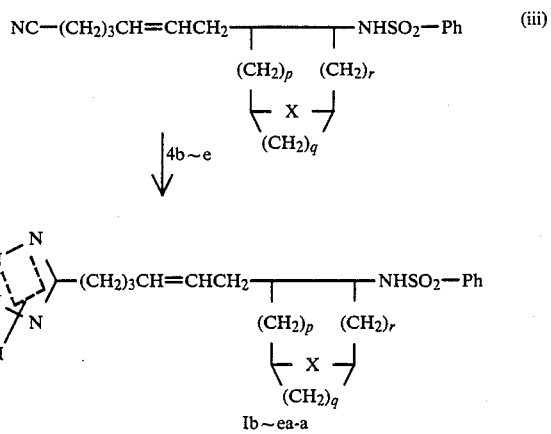

To a solution of [V] mg of nitrile 4b-ea in [W] ml of N-methyl-2-pyrrolidone is added [X] mg of sodium azide and [Y] mg of triethylamine hydrochloride and the mixture is heated in 150° C. oil bath in a nitrogen atmosphere for 15 hours. The reaction mixture is cooled and then added 50 ml of water. The mixture is acidified with 10% hydrochloric acid to pH 1 and extracted with ether. The organic layer is washed with water and extracted with an aqueous solution of 10% sodium hydroxide. The aqueous layer is washed with ether and acidified with 10% hydrochloric acid and extracted with ether again. The organic layer is washed with water, dried over anhydrous sodium sulfate, and evaporated under reduced pressure. The residue is purified by flashed column chromatography ([Z] g of silica gel, 230–400 mesh, hexane-ethyl acetate [f:g→h:i] to give the tetrazole derivatives Ib-ea-a.

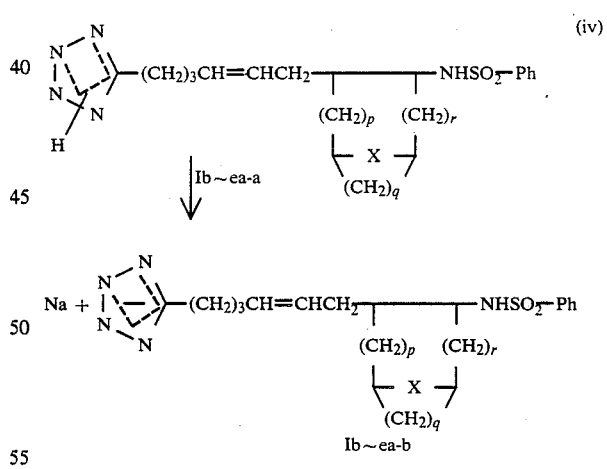

To a solution of Ib-ea-a [j] mg of tetrazole derivative in [k] ml of methanol is added [l] ml of 0.182M sodium methoxide and the mixture is evaporated under reduced pressure. A solution of the residue in [m] ml of water is treated with active carbon and lyophilized to give a sodium salt Ib-ea-b.

TABLE 3 (No. 1)

| Example Number | A | B | C | D | E | F | G |
|---|---|---|---|---|---|---|---|
| 9-(i) | 1.62 | 15 | 2.4 | 15 | 100 | 60 | 0 |
| 10-(i) | 1.13 | 5 | 1.9 | 15 | 100 | 15 | 0 |
| 11-(i) | 1.28 | 35 | 5 | 10 | 150 | 25 | 1 |

TABLE 3 (No. 1)-continued

| Example Number | A | B | C | D | E | F | G |
|---|---|---|---|---|---|---|---|
| 12-(i) | 1.16 | 20 | 5 | 10 | 100 | 20 | 1 |

TABLE 3 (No. 1)

| Example Number | H | I | J | K | L |
|---|---|---|---|---|---|
| 9-(i) | 9 | 1 | 0 | 9 | 1 |
| 10-(i) | 9 | 1 | 0 | 9 | 1 |
| 11-(i) | 1 | 0 | 1 | 2 | 0 |
| 12-(i) | 1 | 0 | 1 | 2 | 0 |

TABLE 3 (No. 2)

| Example Number | M | N | O | P | Q | R | S | T | U |
|---|---|---|---|---|---|---|---|---|---|
| 9-(ii) | 1.0 | 5 | 500 | 610 | 30 | 4 | 1 | 4 | 1 |

TABLE 3 (No. 2)-continued

| Example Number | M | N | O | P | Q | R | S | T | U |
|---|---|---|---|---|---|---|---|---|---|
| 10-(ii) | 0.612 | 3 | 310 | 370 | 15 | 3 | 2 | 3 | 2 |
| 11-(ii) | 1.724 | 6 | 674 | 985 | 25 | 6 | 1 | 2 | 1 |
| 12-(ii) | 0.791 | 5 | 320 | 530 | 25 | 4 | 1 | 2 | 1 |

TABLE 3 (No. 3)

| Example Number | V | W | X | Y | Z | f | g | h | i |
|---|---|---|---|---|---|---|---|---|---|
| 9-(iii) | 740 | 22 | 440 | 470 | 25 | 0 | 1 | 0 | 1 |
| 10-(iii) | 433 | 10 | 257 | 275 | 20 | 0 | 1 | 0 | 1 |
| 11-(iii) | 726 | 18 | 405 | 427 | 20 | 1 | 1 | 1 | 2 |
| 12-(iii) | 658 | 17 | 365 | 387 | 15 | 1 | 1 | 1 | 2 |

TABLE 3 (No. 4)

| Example Number | J | k | l | m |
|---|---|---|---|---|
| 9-(iv) | 504 | 5 | 6.5 | 12 |
| 10-(iv) | 349 | 5 | 4.5 | 8 |
| 11-(iv) | 1079 | 10 | 13.38 | 25 |
| 12-(iv) | 580 | 6 | 7.20 | 13 |

TABLE 4

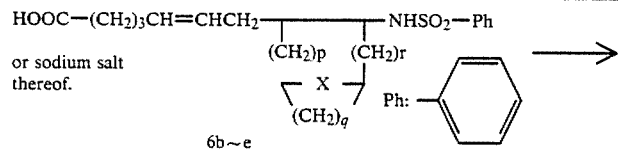

or sodium salt thereof.

6b~e

→

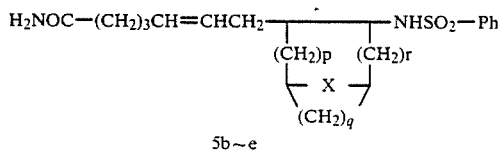

5b~e

| Example Number | Compd. No. | $\begin{array}{c}(CH_2)_p\;(CH_2)_r\\X\\(CH_2)_q\end{array}$ | Yd. (%) | m.p. [°C.] | IR ν max [cm$^{-1}$] | NMR δ ppm | Analysis (Molecular formula) Calcd. (%) Found (%) |
|---|---|---|---|---|---|---|---|
| 9-(i) | 5b | 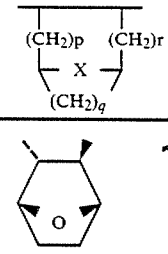 | 66 | 93~96 | (film) 3360, 3200, 1665. | (CDCl$_3$): 1.2-2.2 (11H), 2.22 (2H,t, J=7Hz), 2.90 (1H,dd,J=8, 2Hz), 4.08 (1H,d,J=5Hz), 4.41 (1H,t,J=4Hz), 5.24 (2H,m),5.8-6.1 (3H,m), 7.45-7.65 (3H,m), 7.8-8.0 (2H,m). | (C$_{19}$H$_{26}$N$_2$O$_4$S) C 60.29, H 6.92, N 7.40, S 8.47, C 59.98, H 6.89, N 7.26, S 8.34. |
| 10-(i) | 5c | 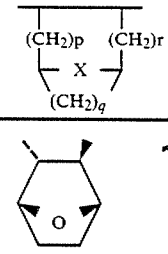 | 64 | | (CHCl$_3$) 3510, 3410, 1676, 1326, 1159. | (CDCl$_3$): 1.2-2.3 (13H), 3.05 (1H,q, J=5Hz), 4.35 (1H,t,J=5Hz), 5.28 (2H,m), 5.73 (1H,s), 5.95 (1H,s), 6.41 (1H,d, J=5Hz), 7.45-7.70 (3H,m), 7.85-8.0 (2H,m). | (C$_{19}$H$_{26}$N$_2$O$_4$S) C 60.29, H 6.92, N 7.40, S 8.47, C 59.55, H 6.87, N 7.23, S 8.21. |

| Example Number | Compd. No. | $\begin{array}{c}(CH_2)_p\;(CH_2)_r\\X\\(CH_2)_q\end{array}$ | Yd. (%) | [α]$_D$ | IR ν max [cm$^{-1}$] | NMR δ ppm | MS [m/z] |
|---|---|---|---|---|---|---|---|
| 11-(i) | 5d | 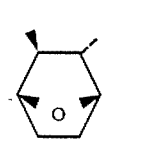 | 95 | −17.5° (24° C., c 0.890, MeOH) | (CHCl$_3$) 3535, 3510, 3420, 3380, 1673, 1329, 1160. | (CDCl$_3$): 0.82 (1H,d,J=10.0Hz), 0.94 (3H,s), 1.16 (3H,s), 1.46 (1H,ddd,J=2.2, 6.2, 14.0Hz), 1.56~2.42 (13H), 3.62 (1H,m), 5.29~5.51 (2H), 5.78 (1H,br.s), 5.86 (1H,d, J=8.5Hz), 5.98 (1H,br.s), 7.45~7.62 (3H), 7.89~7.98 (2H). | 405 (MH$^+$) |
| 12-(i) | 5e | 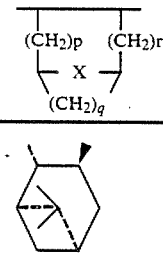 | 76 | +29.3 (24° C., c 1.003, MeOH) | (CHCl$_3$) 3530, 3515, 3420, 3395, 1675, 1321, 1158. | (CDCl$_3$): 0.68 (1H,d,J=10.1Hz), 0.98 (3H,s), 0.99 (3H,s), 1.44 (1H,ddd,J=2.5, 5.5, 13.0Hz), 1.62~2.43 (13H), 3.40 (1H,ddd,J=2.5, 6.0, 7.8Hz), 5.32~5.53 (2H), 5.72 (1H,br. s), 5.91 (1H,d,J=7.6Hz), 6.06 (1H,br.s), 7.44~7.60 (3H), 7.85~7.94 (2H). | 405 (MH$^+$) |

TABLE 5

$$\text{H}_2\text{NOC}-(\text{CH}_2)_3\text{CH}=\text{CHCH}_2-\underset{\underset{(\text{CH}_2)_q}{\overset{(\text{CH}_2)_p}{\mid}}}{\text{(CH)}}-\text{NHSO}_2-\text{Ph} \quad \longrightarrow \quad \text{NC}-(\text{CH}_2)_3\text{CH}=\text{CHCH}_2-\underset{\underset{(\text{CH}_2)_q}{\overset{(\text{CH}_2)_p}{\mid}}}{\text{X}}-\text{NHSO}_2-\text{Ph}$$

5b~e → 4b~ea

| Example Number | Compd. No. | $\underset{\underset{(\text{CH}_2)_q}{\overset{(\text{CH}_2)_p}{\mid}}}{\text{(CH)}}$ | Yd. (%) | $[\alpha]_D$ | IR ν max [cm$^{-1}$] | NMR δ ppm | Analysis (Molecular Formula) Calcd. (%) Found (%) |
|---|---|---|---|---|---|---|---|
| 9-(i) | 4ba |  | 84 | | (film) 3270, 2240, 1328, 1161. | (CDCl$_3$): 1.2–2.2 (11H), 2.35 (2H,t,J=6Hz), 2.96 (1H,dd,J=4, 9Hz), 4.01 (1H,d,J=5Hz), 4.41 (1H, J=5Hz), 4.96 (1H,d,J=9Hz), 5.24 (2H,m) 7.5–7.7 (3H,m), 7.8–8.1 (2H,m). | (C$_{19}$H$_{24}$N$_2$O$_3$S) C 63.31, H 6.71, N 7.77, S 8.89, C 63.21, H 6.49, N 7.72, S 8.73. |
| 10-(i) | 4ca |  | 80 | | (film) 3270, 2250, 1328, 1163. | (CDCl$_3$): 1.8–2.2 (11H), 2.29 (2H,t,J=7Hz), 3.01 (1H,q,J=5Hz), 4.11 (1H,d,J=5H), 4.45 (1H,t, J=5Hz), 5.20 (2H,m), 7.5–7.7 (3H,m), 7.85–7.95 (2H,m). | (C$_{19}$H$_{24}$N$_2$O$_3$S) C 63.31, H 6.71, N 7.77, S 8.89, C 62.79, H 6.68, N 7.70, S 8.69 |

| Example Number | Compd. No. | $\underset{\underset{(\text{CH}_2)_q}{\overset{(\text{CH}_2)_p}{\mid}}}{\text{(CH)}}$ | Yd. (%) | $[\alpha]_D$ | IR ν max [cm$^{-1}$] | NMR δ ppm | Analysis (Molecular formula) Calcd. (%) Found (%) |
|---|---|---|---|---|---|---|---|
| 11-(i) | 4da |  | 80 | −15.3° (24° C., c 0.990, MeOH) | (film) 3280, 2245, 1330, 1160. | (CDCl$_3$): 0.78 (1H,d,J=10.0Hz), 0.95 (3H, s), 1.17 (3H,s), 1.52 (1H,ddd,J=2.2, 6.0, 14.0Hz), 1.60–2.43 (11H), 2.33 (2H,t, J=7.2Hz), 3.62 (1H,m), 4.67 (1H,d, J=8.8Hz), 5.20–5.43 (2H), 7.47–7.64 (3H), 7.88–7.97 (2H). | (C$_{22}$H$_{30}$N$_2$O$_3$S) C 68.36, H 7.82, N 7.25, S 8.30, C 68.03, H 7.79, N 7.14, S 8.18. |
| 12-(i) | 4ea |  | 93 | +31.7° (24° C., c 1.434, MeOH) | (film) 3290, 2240, 1322, 1161. | (CDCl$_3$): 0.74 (1H,d,J=10.3Hz), 1.00 (3H, s), 1.09 (3H,s), 1.42 (1H,ddd,J=2.2, 5.1, 13.2Hz), 1.66–2.28 (11H), 2.33 (2H,t, J=7.1Hz), 3.38 (1H,ddd,J=2.5, 5.3, 8.4Hz), 4.72 (1H,d,J=8.4Hz), 5.23–5.47 (2H), 7.46–7.63 (3H), 7.84–7.93 (2H). | (C$_{22}$H$_{30}$N$_2$O$_3$S) C 68.36, H 7.82, N 7.25, S 8.30, C 67.91, H 7.76, N 7.15, S 8.29, [MS(m/z)]: 387 (MH$^+$)] |

TABLE 6

NC—(CH₂)₃CH=CHCH₂—[(CH₂)p—X—(CH₂)q—(CH₂)r]—NHSO₂—Ph ⟶ H—[triazole]—(CH₂)₃CH=CHCH₂—[(CH₂)p—X—(CH₂)q—(CH₂)r]—NHSO₂—Ph 4b~ea  →  Ib~e-a

| Example Number | Compd. No. | (CH₂)p—X—(CH₂)q—(CH₂)r | Yd. (%) | IR ν max [cm⁻¹] | NMR δ ppm | MS (m/z) |
|---|---|---|---|---|---|---|
| 9-(iii) | I$^{ba\text{-}a}$ | (cyclohexane with O) | 61 | (CHCl₃) 3220, 1326, 1158. | (CDCl₃): 1.1~2.2(11H), 2.91(1H,d,J=5Hz), 3.02(2H,t, J=7Hz), 4.05(1H,d,J=4Hz), 4.42(1H,s), 5.23(2H,m), 5.72 (1H,d,J=8Hz), 7.45~7.71(3H,m), 7.8~7.95(2H,m). | 404 (MH⁺) |
| 10-(iii) | I$^{ca\text{-}a}$ | (cyclohexane with O) | 78 | (CHCl₃) 3270, 1327, 1162. | (CDCl₃): 1.35~2.1(11H), 2.98(2H,t,J=6Hz), 3.16(1H,d, J=4Hz), 4.20(1H,d,J=5Hz), 4.42(1H,t,J=5Hz), 5.26(2H,m), 5.85(1H,d,J=5Hz), 7.45~7.65(3H,m), 7.85~7.95(2H,m). | 404 (MH⁺) |

| Example Number | Compd. No. | (CH₂)p—X—(CH₂)q—(CH₂)r | Yd. (%) | [α]$_D$ | IR ν max [cm⁻¹] | NMR δ ppm | Analysis (Molecular formula) Calcd. (%) Found (%) or MS |
|---|---|---|---|---|---|---|---|
| 11-(iii) | I$^{da\text{-}a}$ | (pinane) | 86 | −18.8° (24° C., c 1.072, MeOH) | 3370, 3240, 1551, 1328, 1158. | (CDCl₃): 0.79(1H,d,J=9.9Hz), 0.91(3H,s), 1.15 (3H,s), 1.43(1H,ddd,J=2.0, 6.4, 14.0Hz), 1.65~ 2.52(11H), 3.40(2H,dd,J=7.4, 8.2Hz), 3.68(1H, ddd,J=7.0, 9.3, 16.0Hz), 5.31~5.58(3H), 7.49~7.66(3H), 7.92~8.01(2H). | (C₂₂H₃₁N₅O₂S) C 61.51, H 7.27, N 16.30, S 7.46, C 61.16, H 7.23, N 16.03, S 7.33 |
| 12-(iii) | I$^{ea\text{-}a}$ | (pinane) | 84 | +25.2° (24° C., c 1.007, MeOH) | 3395, 3260, 1552, 1327, 1159. | (CDCl₃): 0.70(1H,d,J=10.3Hz), 0.96(3H,s), 1.02 (3H,s), 1.48(1H,ddd,J=2.6, 4.5, 13.2Hz), 1.71(1H, m), 1.78~2.26(9H), 2.39(1H,m), 3.06(2H,t,J= 7.5Hz), 3.43(1H,ddd,J=2.6, 5.5, 8.3Hz), 5.16(1H, J=8.3Hz), 5.44(2H,m), 7.48~7.66(3H), 7.84~7.93 (2H). | (m/z): 430 (MH³⁰) |

TABLE 7

H—[triazole]—(CH₂)₃CH=CHCH₂—[(CH₂)p—X—(CH₂)q—(CH₂)r]—NHSO₂—Ph  ⟶

Ib~e-a

H—[triazole] Na⁺ —(CH₂)₃CH=CHCH₂—[(CH₂)p—X—(CH₂)q—(CH₂)r]—NHSO₂—Ph

Ib~e-b

| Example Number | Compd. No. | (CH₂)p—X—(CH₂)q—(CH₂)r | IR ν max (KBr) | Analysis (Molecular formula) Calcd. (%) Found (%) |
|---|---|---|---|---|

TABLE 7-continued

| | | | | |
|---|---|---|---|---|
| 9-(iv) | I$^{ba\text{-}b}$ | | 1325, 1160. | (C$_{19}$H$_{24}$N$_5$O$_3$SNa.1.2H$_2$O)<br>C 51.04, H 5.95, N 15.66, S 7.17,<br>C 51.28, H 6.02, N 15.62, S 7.36. |
| 10-(iv) | I$^{ca\text{-}b}$ | | 1324, 1162. | (C$_{19}$H$_{24}$N$_5$O$_3$SNa.0.4H$_2$O)<br>C 52.74, H 5.78, N 16.19, S 7.41,<br>C 52.91, H 5.94, N 16.15, S 7.57. |
| 11-(iv) | I$^{da\text{-}b}$ | | 3280, 1324, 1161. | (C$_{22}$H$_{30}$N$_5$O$_2$SNa.0.7H$_2$O)<br>C 56.93, H 6.82, N 15.09, S 6.91, H$_2$O 2.72,<br>C 56.65, H 6.82, N 15.00, S 6.95, H$_2$O 2.80. |
| 12-(iv) | I$^{ea\text{-}b}$ | | 3300, 1322, 1160. | (C$_{22}$H$_{30}$N$_5$O$_2$SNa.0.7H$_2$O)<br>C 56.93, H 6.82, N 15.09, S 6.91, H$_2$O 2.72,<br>C 56.74, H 6.89, N 14.94, S 6.77, H$_2$O 2.49. |

Preparation of Intermediate 2

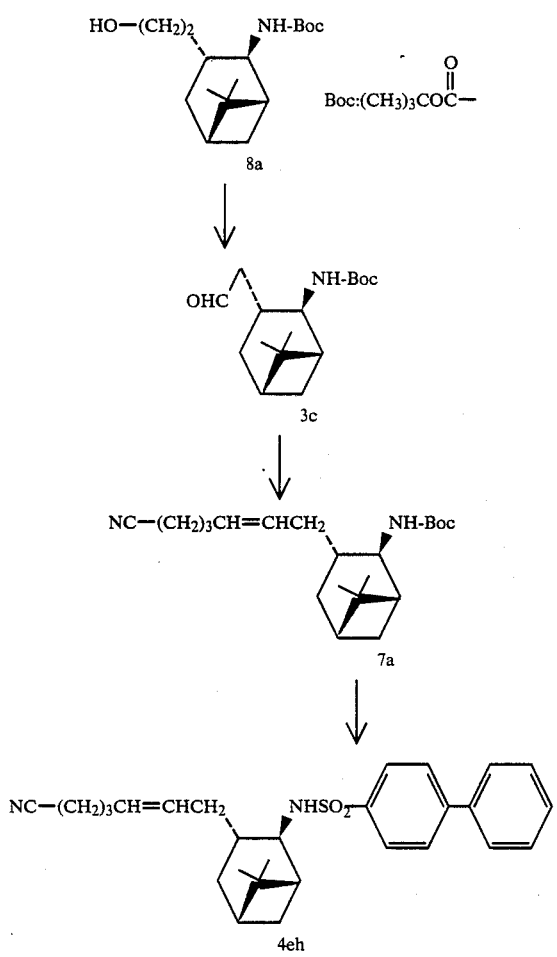

(1) (+)-2-[(1S,2R,3S,5S)-2-tert-butoxycarbonylamino-6,6-dimethylbicyclo [3.1.1]hept-3-yl]-ethanol 8a
(2) (1S,2R,3S,5S)-2-tert-butoxycarbonylamino-3-formylmethyl-6,6-dimethylbicyclo [3.1.1]heptane 3c
(3) (1R,2R,3S,5S)-2-tert-butoxycarbonylamino)-3-[(2Z)-6-cyano-2-hexenyl]-6,6-dimethylbicyclo [3.1.1]heptane 7a
(4) (1R,2R,3S,5S)-2-(4-biphenylylsulfonylamino)-3-[(2Z)-6-cyano-2-hexenyl]-6,6-dimethylbicyclo [3.1.1]heptane 4ea (i) To a solution of 8 ml of oxalyl chloride in 100 ml of dichloromethane is added a solution of 13.6 ml of dimethyl sulfoxide in 30 ml of dichloromethane at −78° C. under stirring and the mixture is stirred for 5 minutes. A solution of 13.53 g of (+)-2-[(1S,2R,3R,5S)-2-tert-butoxycarbonylamino-6,6-dimethylbicyclo [3.1.1]hept-3-ethanol 8a in 50 ml of dichloromethane is dropwise added thereto at −78° C. under stirring and the resulting solution is stirred at the same temperature for 30 minutes. After 50 ml of triethylamine is dropwise added at −78° C., the mixture is warmed to room temperature. The reaction mixture is washed with water and dried over anhydrous sodium sulfate, and evaporated under reduced pressure to give a crude aldehyde.

To a suspension of 30.3 g of (4-cyanobutyl)triphenylphosphonium bromide in 140 ml of tetrahydrofuran is added 8.07 g of potassium-tert-butoxide under stirring in an nitrogen atmosphere and the mixture is stirred at room temperature for 1.5 hours. A solution of the above prepared crude aldehyde 3c in 50 ml of tetrahydrofuran is dropwise added at 0° C. and the resulting mixture is stirred at the same temperature for 1 hour. Water is added to the reaction mixture, then which is extracted with ether. The organic layer is washed with water, dried over anhydrous sodium sulfate, and evaporated under reduced pressure. The residue is purified by flash chromatography on 200 g of silica gel (hexane:ethyl acetate=6:1) to give 6.9 g of the titled compound 7a in 41.8% yield.

The physical constants of the compound 7a:
[α]$_D$+39.8(24° C., c=1.205, MeOH),
IRνmax(film)3460, 3375, 2245, 1710cm$^{-1}$.
NMR(CDCl$_3$)δ ppm: 0.85(1H, d, J=10 Hz), 1.03 (3H, s), 1.21(3H, s), 1.39~1.54(1H, m), 1.44 (9H, s), 1.66~2.48(11H), 2.35(2H, t, J=7 Hz), 3.76(1H, m), 4.64(1H, d, J=9 Hz), 5.21~5.61(2H).

Anal. Calcd. (%) for $C_{21}H_{34}N_2O_2$: C, 72.79: ; H, 9.89; N, 8.08 Found: C, 72.45; H, 9.90; N, 8.16.

(ii) To a solution of 690 mg of the nitrile 7a in 2 ml of dichloromethane is added 2 ml of trifluoroacetic acid at 0° C. and the mixture is stirred at the same temperature for 1.5 hours. The solvent is evaporated under reduced pressure. A solution of the residue in ether is washed with 10% sodium carbonate and water, successively, dried over anhydrous sodium sulfate, and evaporated under reduced pressure to give a crude amine. To a solution of the amine in 10 ml of dichloromethane is added 0.4 ml of triethylamine and 510 mg of 4-biphenylylsulfonyl chloride and the mixture is stirred at room temperature for 1.5 hours. The solvent is evaporated under reduced pressure to give a residue, of which solution in ether is washed with 10% hydrochloric acid and water, successively, dried over anhydrous sodium sulfate, and evaporated. The residue is purified by frash chromatography on 25 g of silica gel (hexane:ethyl acetate=4:1) to give 607 mg of the sulfonamido derivative 4eh in 65.9% yield. The physical constants are shown in Table 8.

Preparation of Intermediates 3 to 8

The reaction may be proceed by the same procedure as in Preparation of Intermediate 1 except using 2-naphthylsulfonyl chloride, 4-methyophenylsulfonyl chloride, 4-chlorophenylsulfonyl chloride, 3-chlorophenylsulfonyl chloride, 2-chlorophenylsulfonyl chloride, p-tolylsulfonyl chloride, or 4-bromophenylsulfonyl chloride instead of 4-biphenylylsulfonyl chloride.

The physical constants of the products are shown in Table 8.

TABLE 8

$NC-(CH_2)_3CH=CHCH_2$ ... $NHSO_2-R$

4e

| Prptn. Intmt. No. | Compd. No. | R | Yd. (%) | $[\alpha]_D$ (25° C., CH$_3$OH) | IR$\nu$max (CHCl$_3$) [cm$^{-1}$] | NMR δ ppm (CDCl$_3$) | MS m/z(M$^+$) |
|---|---|---|---|---|---|---|---|
| 2 | 4eh | 4-biphenylyl | 65.9 | +31.3 (c = 0.896) | 3390 2245 1332 1158 | 0.76(1H, d, J=10Hz), 1.03(3H, s), 1.11(3H, s), 1.43(1H, m), 1.69(2H, m), 1.81~2.34(9H), 2.28 (2H, t, J=7Hz), 3.42(1H, m), 4.74(1H, d, J=9Hz), 5.28(1H, dd, J=7, 11Hz), 5.39(1H, dd, J=6, 11Hz), 7.36~7.54(3H), 7.63(2H, dd, J=2, 8Hz), 7.73(2H, t, J=9Hz), 7.94(2H, d, J=9Hz). | 462 |
| 3 | 4ei | 2-naphthyl | 68.0 | +13.7 (c = 1.200) | 3390 2245 1333 1154 | 0.73(1H, d, J=10Hz), 1.03(3H, s), 1.08(3H, s), 1.41(1H, m), 1.57(2H, m), 1.78~2.27(8H), 2.20 (2H, t, J=7Hz), 3.42(1H, ddd, J=3, 5, 9Hz), 4.84(1H, d, J=9Hz), 5.13~5.42(2H), 7.64(2H, m), 7.81~8.01(4H), 8.45(1H, d, J=1Hz). | 436 |
| 4 | 4ee | 4-methoxyphenyl | 60.2 | +27.1 (c = 1.418) | 3395 2250 1332 1155 | 0.73(1H, d, J=10Hz), 1.01(3H, s), 1.11(3H, s), 1.42(1H, ddd, J=2, 5, 13Hz), 1.71(2H, m), 180~2.39(9H), 2.34(2H, t, J=7Hz), 3.33(1H, ddd, J=3, 6, 8Hz), 3.88(3H, s), 4.66(1H, d, J=8Hz), 5.24~5.48(2H), 6.97(2H, d, J=9Hz), 7.80(2H, d, J=9Hz). | 416 |
| 5 | 4ej | 4-chlorophenyl | 57.3 | +31.4 (c = 1.542) | 3395 2245 1341 1160 | 0.75(1H, d, J=10Hz), 1.01(3H, s), 1.12(3H, s), 1.44(1H, ddd, J=3, 5, 13Hz), 1.72(2H, m), 1.81~2.37(9H), 2.35(2H, t, J=7Hz), 3.37(1H, ddd, J=3, 6, 8Hz), 4.77(1H, d, J=8Hz), 5.24~5.48 (2H), 7.49(2H, d, J=9Hz), 7.82(2H, d, J=9Hz). | 420 |
| 6 | 4ek | 3-chlorophenyl | 60.2 | +29.5 (c = 1.108) | 3390 2245 1342 1160 | 0.76(1H, d, J=10Hz), 1.02(3H, s), 1.44(1H, m), 1.73(2H, m), 1.81~2.37(9H), 2.35(2H, t, J=7Hz), 3.39(1H, m), 4.83(1H, d, J=8Hz), 5.36(2H, m), 7.46(1H, m), 7.55(1H, m), 7.76(1H, m), 7.88(1H, m). | 420 |
| 7 | 4el | 2-chlorophenyl | 59.6 | -16.6 (c = 1.458) | 3390 2250 1347 1167 | 0.71(1H, d, J=10Hz), 1.08(3H, s), 1.11(3H, s), 1.42(1H, m), 1.73(2H, m), 1.82~2.40(9H), 2.36 (2H, t, J=7Hz), 3.39(1H, ddd, J=3, 5, 9Hz), 5.25(1H, d, J=9Hz), 5.20~5.48(2H), 7.38~7.57 (3H), 8.10(1H, m). | |
| 8 | 4eb | p-tolyl | 64.9 | +28.8 (c = 1.020) | 3390 2250 1325 1158 | 0.74(1H, d, J=10Hz), 1.01(3H, s), 1.10(3H, s), 1.42(1H, ddd, J=3, 5, 13Hz), 1.7(2H, m), 1.80~2.45(9H), 2.34(2H, t, J=7Hz), 2.43(3H, s), 3.36(1H, ddd, J=3, 5, 8Hz), 4.65(1H, d, J=8Hz), 5.24~5.48(2H), 7.30(2H, d, J=8Hz), 7.75(2H, d, J=8Hz). | 400 |

EXAMPLE 13 to 19

$NC-(CH_2)_3CH=CHCH_2$ ... $NHSO_2-R$

4eb~1
(i)

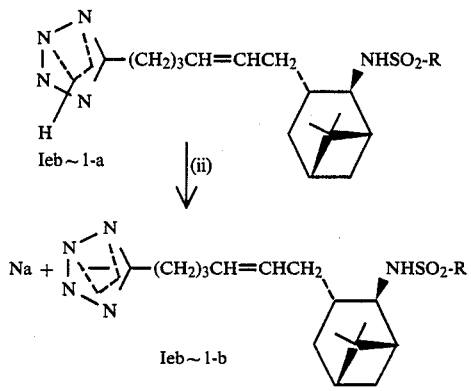

EXAMPLE 13

(R:4-biphenylyl)

Preparation of (1R,2R,3S,5S)-2-[(4-biphenylyl)sulfonylamino]-3-[(2Z)-6-(5-tetrazolyl) hex-2-enyl]-6,6-dimethylbicyclo[3.1.1]heptane Ieh-a and its sodium salt Ieh-b.

EXAMPLE 14

(R:2-naphthyl)

Preparation of (1R,2R,3S,5S)-2-[(2-naphthyl)sulfonylamino]-3-[(2Z)-6-(5-tetrazolyl) hex-2-enyl]-6,6-dimethylbicyclo[3.1.1]-heptane Iei-a and its sodium salt Iei-b.

EXAMPLE 15

(R:4-methoxyphenyl)

Preparation of (1R,2R,3S,5S)-2-[(4-methoxyphenyl)sulfonylamino]-3-[(2Z)-6-(5-tetrazolyl) hex-2-enyl]-6,6-dimethylbicyclo [3.1.1]heptane Iee-a and its sodium salt Iee-b.

EXAMPLE 16

(R:4-chlorophenyl)

Preparation of (1R,2R,3S,5S)-2-[(4-chlorophenyl)sulfonylamino]-3-[(2Z)-6-(5-tetrazolyl) hex-2-enyl]-6,6-dimethylbicyclo [3.1.1]heptane Iej-a and its sodium salt Iej-b.

EXAMPLE 17

(R:3-chlorophenyl)

Preparation of (1R,2R,3S,5S)-2-[(3-chlorophenyl)sulfonylamino]-3-[(2Z)-6-(5-tetrazolyl) hex-2-enyl]-6,6-dimethyl-bicyclo [3.1.1]heptane Iek-a and its sodium salt Iek-b.

EXAMPLE 18

(R:2-chlorophenyl)

Preparation of (1R,2R,3S,5S)-2-[(2-chlorophenyl)sulfonylamino]-3-[(2Z)-6-(5-tetrazolyl) hex-2-enyl]-6,6-dimethylbicyclo [3.1.1]heptane Iel-a and its sodium salt Iel-b.

EXAMPLE 19

(R:p-tolyl)

Preparation of (1R,2R,3S,5S)-2-(p-tolylsulfonylamino)-3-[(2Z)-6-(5-tetrazolyl) hex-2-enyl]-6,6-dimethylbicyclo[3.1.1]-heptane Ieb-a and its sodium salt Ieb-b.

The nitriles 4eb-1 prepared in Preparation of Intermediates 2 to 8 are allowed to react and post-treated according to the general procedure of Example 9 to 12-(iii) and (ii) under the reaction condition shown in Table 9. The yield and physical constants of the product are shown in Tables 10 and 11.

TABLE 9

| Ex. No. | V | W | X | Y | Z | f | g | h | i |
|---|---|---|---|---|---|---|---|---|---|
| 13-(i) | 507 | 10 | 300 | 320 | 25 | 1 | 1 | 0 | 1 |
| 14-(i) | 535 | 10 | 319 | 337 | 25 | 1 | 1 | 0 | 1 |
| 15-(i) | 466 | 10 | 291 | 308 | 25 | 1 | 1 | 0 | 1 |
| 16-(i) | 416 | 10 | 257 | 272 | 25 | 1 | 1 | 0 | 1 |
| 17-(i) | 440 | 10 | 272 | 288 | 25 | 1 | 1 | 0 | 1 |
| 18-(i) | 433 | 10 | 267 | 283 | 25 | 1 | 1 | 0 | 1 |
| 19-(i) | 442 | 10 | 287 | 304 | 25 | 1 | 1 | 0 | 1 |

TABLE 9 (No. 2)

| Ex No. | j | k | l | m |
|---|---|---|---|---|
| 13-(ii) | 290 | 5 | 3.11 | 6 |
| 14-(ii) | 380 | 5 | 4.14 | 8 |
| 15-(ii) | 292 | 5 | 3.32 | 6 |
| 16-(ii) | 246 | 5 | 2.77 | 5 |
| 17-(ii) | 338 | 5 | 3.80 | 6.5 |
| 18-(ii) | 335 | 5 | 3.77 | 6.5 |
| 19-(ii) | 333 | 5 | 3.92 | 6.5 |

TABLE 10

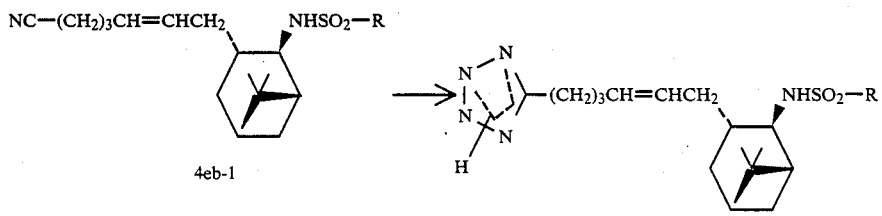

| Ex. No. | Compd. No. | R | Yd. (%) | $[\alpha]_D$ (25° C., CH$_3$OH) | IRνmax [cm$^{-1}$] | NMR δ ppm (CDCl$_3$) | MS m/z |
|---|---|---|---|---|---|---|---|
| 13-(i) | Ieh-a | 4-biphenylyl | 75.8 | +25.0 (c = 1.048) | (KBr) 3330 3280 1328 1161 | 0.72(1H, d, J=10Hz), 0.99(3H, s), 1.04(3H, s), 1.51(1H, m), 1.72~2.38(10H), 2.45(1H, m), 3.06 (2H, t, J=8Hz), 3.48(1H, m), 5.14(1H, d, J=8Hz), 5.46(2H, m), 5.60(1H, br. s), 7.38~7.54(3H), 7.62(2H, dd, J=2, 8Hz), 7.75(2H, d, J=9Hz), 7.95(2H, d, J=9Hz). | 505 m.p. 89~92° C. |

TABLE 10-continued

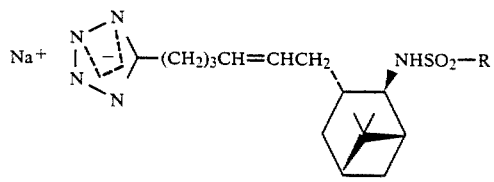

| Ex. No. | Compd. No. | R | Yd. (%) | [α]_D (25° C., CH3OH) | IR νmax [cm^-1] | NMR δ ppm (CDCl3) | MS m/z |
|---|---|---|---|---|---|---|---|
| 14-(i) | Iei-a | 2-naphthyl | 73.1 | +10.4 (c = 0.883) | (CHCl3) 3395, 3230, 1326, 1154 | 0.69(1H, d, J=10Hz), 0.97(3H, s), 0.98(3H, s), 1.48(1H, m), 1.68~2.22(10H), 2.44(1H, m), 3.05 (2H, t, J=7Hz), 3.48(1H, m), 5.25(1H, d, J=8Hz), 5.43(2H, m), 5.75(1H, br. s), 7.64(2H, m), 7.78~8.04(4H), 8.46(1H, d, J=2Hz). | 480(MH+) |
| 15-(i) | Iee-a | 4-methoxyphenyl | 64.6 | +20.8 (c = 1.259) | (CHCl3) 3385, 3220, 1326, 1150 | 0.70(1H, d, J=10Hz), 0.97(3H, s), 1.05(3H, s), 1.48(1H, ddd, J=3, 5, 14Hz), 1.75(1H, m), 1.80~2.26(9H), 2.39(1H, m), 3.06(2H, t, J=8Hz), 3.37(1H, ddd, J=3, 5, 8Hz), 3.88(3H, s), 5.13 (1H, d, J=8Hz), 5.43(2H, m), 6.99(2H, d, J=9Hz), 7.81(2H, d, J=9Hz), 8.90(1H, br. s). | 460(MH+) |
| 16-(i) | Iej-a | 4-chlorophenyl | 55.7 | +25.5 (c = 1.194) | (CHCl3) 3395, 3260, 1330, 1160 | 0.71(1H, d, J=11Hz), 0.97(3H, s), 1.06(3H, s), 1.50(1H, ddd, J=2, 4, 13Hz), 1.67~2.30(10H), 2.42(1H, m), 3.06(2H, t, J=7Hz), 3.42(1H, ddd, J=3, 5, 9Hz), 5.16(1H, d, J=9Hz), 5.42(2H, m), 5.78(1H, br. s), 7.51(2H, d, J=9Hz), 7.82(2H, d, J=9Hz). | 464(MH+) |
| 17-(i) | Iek-a | 3-chlorophenyl | 77.9 | +25.3 (c = 1.251) | (CHCl3) 3390, 3270, 1330, 1159 | 0.72(1H, d, J=10Hz), 0.97(3H, s), 1.06(3H, s), 1.48(1H, ddd, J=3, 5, 14Hz), 1.70~2.45(11H), 3.07(2H, t, J=8Hz), 3.43(1H, ddd, J=2, 5, 8Hz), 5.28~5.51(3H), 7.48(1H, t, J=8Hz), 7.57(1H, td, J=2, 8Hz), 7.78(1H, td, J=2, 8Hz), 7.87 (1H, t, J=2Hz), 9.10(1H, br. s). | 464(MH+) |
| 18-(i) | Iel-a | 2-chlorophenyl | 79.9 | −15.9 (c = 1.355) | (CHCl3) 3385, 3235, 1333, 1161 | 0.68(1H, d, J=10Hz), 1.05(6H, s), 1.48(1H, m), 1.56(1H, m), 1.83~2.30(9H), 2.43(1H, m), 3.08 (2H, t, J=8Hz), 3.41(1H, ddd, J=3, 5, 9Hz), 5.41(1H, d, J=9Hz), 5.45(2H, m), 7.40~7.52(1H, m), 7.55(2H, m), 7.78(1H, br. s), 8.10(1H, m). | 464(MH+) |
| 19-(i) | Ieb-a | p-tolyl | 78.7 | +21.8 (c = 1.136) | (CHCl3) 3395, 3240, 1328, 1158 | 0.70(1H, d, J=10Hz), 0.96(3H, s), 1.03(3H, s), 1.48(1H, ddd, J=3, 5, 14Hz), 1.73(1H, m), 1.78~2.28(9H), 2.41(1H, m), 2.44(3H, s), 3.06(2H, t, J=8Hz), 3.40(1H, ddd, J=2, 5, 8Hz), 5.13 (1H, d, J=8Hz), 5.44(2H, m), 7.32(2H, d, J=8Hz), 7.76(2H, d, J=8Hz), 7.85(1H, br. s). | 444(MH+) |

TABLE 9 (No. 2)

| Ex No. | j | k | l | m |
|---|---|---|---|---|
| 13-(ii) | 290 | 5 | 3.11 | 6 |
| 14-(ii) | 380 | 5 | 4.14 | 8 |
| 15-(ii) | 292 | 5 | 3.32 | 6 |
| 16-(ii) | 246 | 5 | 2.77 | 5 |
| 17-(ii) | 338 | 5 | 3.80 | 6.5 |
| 18-(ii) | 335 | 5 | 3.77 | 6.5 |
| 19-(ii) | 333 | 5 | 3.92 | 6.5 |

TABLE 11

| Example Number | Compd. No. | R | IR ν max (KBr) [cm^-1] | Analysis Calcd. (%) Found (%) |
|---|---|---|---|---|
| 13-(ii) | Ieh-b | 4-biphenylyl | 3380, 3280, 1320, 1157 | C28H34N5O2SNa·H2O C, 61.63; H, 6.65; N, 12.83; S, 5.88 C, 61.66; H, 6.42; N, 12.91; S, 5.99 |
| 14-(ii) | Iei-b | 2-naphthyl | 3390, 3300, 1322 | C26H32N5O2SNa·1.2H2O C, 59.68; H, 6.63; N, 13.38; S, 6.13 C, 59.43; H, 6.48; N, 13.34; S, 6.32 |

TABLE 11-continued

| Example Number | Compd. No. | R | IR ν max (KBr) [cm⁻¹] | Anaylsis Calcd. (%) Found (%) |
|---|---|---|---|---|
| 15-(ii) | Iee-b | 4-methoxy-phenyl | 1158 3400 3280 1320 1151 | $C_{23}H_{32}N_5O_3SNa \cdot 0.9H_2O$<br>C, 55.49; H, 6.84; N, 14.07; S, 6.44<br>C, 55.50; H, 6.64; N, 14.05; S, 6.34 |
| 16-(ii) | Iej-b | 4-chloro-phenyl | 3410 3290 1322 1161 | $C_{22}H_{29}ClN_5O_2SNa \cdot H_2O$<br>C, 52.43; H, 6.20; Cl, 7.03;<br>N, 13.89; S, 6.36<br>C, 52.13; H, 5.98; Cl, 6.88;<br>N, 13.94; S, 6.54 |
| 17-(ii) | Iek-b | 3-chloro phenyl | 3400 3285 1330 1161 | $C_{22}H_{29}ClN_5O_2SNa \cdot H_2O$<br>C, 52.43; H, 6.20; Cl, 7.03;<br>N, 13.89; S, 6.36<br>C, 52.52; H, 6.12; Cl, 6.99;<br>N, 14.03; S, 6.48 |
| 18-(ii) | Iel-b | 2-chloro phenyl | 3380 3320 1332 1163 | $C_{22}H_{29}ClN_5O_2SNa \cdot 0.7H_2O$<br>C, 52.99; H, 6.15; Cl, 7.11;<br>N, 14.05; S, 6.43<br>C, 52.92; H, 6.13; Cl, 6.64;<br>N, 14.05; S, 6.47 |
| 19-(ii) | Ieb-b | p-tolyl | 3425 3290 1320 1158 | $C_{23}H_{32}N_5O_2SNa \cdot 0.9H_2O$<br>C, 57.34; H, 7.07; N, 14.54;<br>S, 6.66<br>C, 57.40; H, 6.82; N, 14.58;<br>S, 6.56 |

EXAMPLE 20

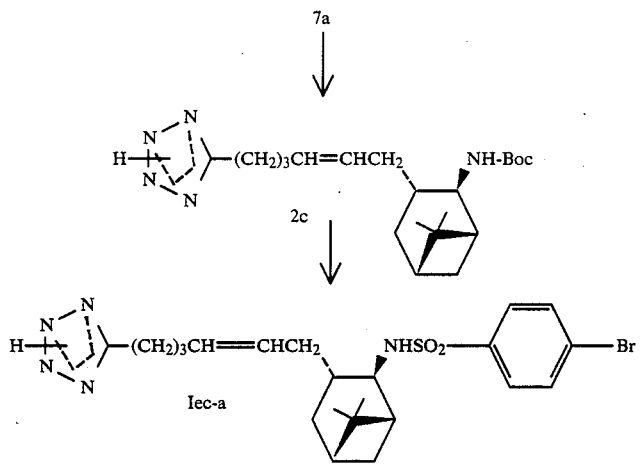

Iec-b: Sodium salt of Iec-a (1) The compound 7a prepared in Preparation of Intermediate 2-(3)
(2) (1R,2R,3S,5S)-2-tert-butoxycarbonylamino-3-[(2Z)-6-(5-tetrazolyl) hex-2-enyl]-6,6-dimethylbicylo[3.1.1]heptane 2c
(3) (1R,2R,3S,5S)-2-[(4-bromophenyl)sulfonylamino]-3-[(2Z)-6-(5-tetrazolyl) hex-2-enyl]-6,6-dimethylbicyclo[3.1.1]heptane Iec-a and its sodium salt Iec-b The compound 7a is allowed to react in the same procedure as in Examples 9 to 12-(iii) to give the compound 2c.

Yield: 58.7%,
$[α]_D$: +37.9 (25° C., c=0.979, CH₃OH),

IRνmax(film): 3460, 3340, 3135, 1661cm⁻¹.
NMRδ ppm (CDCl₃): 0.64(1H, d, J=10 Hz), 1.03 (3H, s), 1.23(3H, s), 1.38~1.52(1H, m), 1.46 (9H, s), 1.70~2.35(11H), 2.88~3.12(2H), 3.47(1H, ddd, J=3, 6, 9 Hz), 4.82(1H, d, J=9 Hz), 5.28~5.52(2H).
MS(m/z): 390(MH+), The prepared compound 2c is treated by the same procedure as in Preparation of Intermediate 2-(ii) and the sulfonylamino moiety at tetrazole of the resulting di-4-bromophenylsulfonamide is removed by treatment with sodium hydroxide.

Yield of the compound Iec-a: 30.2%.
$[\alpha]_D$: +25.9(25° C., c=1.018, $CH_3OH$),
IR$\nu$max(KBr):3395, 3265, 1330, 1158$cm^{-1}$.
NMR$\delta$ ppm($CHCl_3$): 0.72(1H, d, J=10 Hz), 0.97 (3H, s), 1.06(3H, s), 1.5 0(1H, ddd, J=3, 5, 13 Hz), 1.73(1H, m), 1.78~2.30(9H), 2 .42(1H, m), 3.06(2H, t, J=8 Hz), 3.42(1H, ddd, J=2, 5, 8 Hz), 5 .44(2H, m), 7.63~7.79(4H).
MS: 508, 510(MH+).

The compound Iea-a is treated by the same manner as in Example 1-(iv) to give its sodium salt Iec-b.
IR$\nu$max(KBr) : 3430, 3290, 1322, 1160$cm^{-1}$.
Anal. Calcd. (%) for $C_{22}H_{29}BrN_5O_2SNa·0.9H_2O$: C, 48.34; H, 5.68; Br, 14.62; N, 12.81; S, 5.87; Found (%): C, 48.42; H, 5.70; Br, 14.27; N, 12.07; S, 5.64.

Experiment 1

The compounds of the present invention have a potent antagonistic action against thromboxane $A_2$ receptor, and strongly inhibit platelet aggregation or vasoconstriction caused by thromboxane $A_2$. This means that the compounds of this invention are expected to be used as anti-thrombotic and anti-vasoconstriciting drugs. The platelet aggregation inhibitory activity is shown in the following in vitro rat washed platelet aggregation test exhibited by representative compounds of the present invention.

Material and Method

From the abdominal artery of a male rat (Sprague-Dowley, 8 weeks old) was collected 10 ml of blood with a syringe containing 1.5 ml of ACD (85 mM of sodium citrate, 70 mM of citric acid, 110 mM of glucose) and 20 $\mu$g of prostaglandin $E_1$. The blood is placed in a plastic test tube, shaken moderately turning and centrifuged for 10 minutes at 160×g to give platelet rich plasma (PRP). To the prepared PRP was added apyrase (25 $\mu$g/ml) and the mixture was layered on 40% bovine serum albumin. The resulting mixture is centrifuged at 1200×g for 25 minutes. The platelet pellet suspended in a small amount of a buffer (137 mM of NaCl, 2.7 mM of KCl, 1.0 mM of $MgCl_2$, 3.8 mM of $NaH_2PO_4$, 3.8 mM of Hepes, 5.6 mM of glucose, 0.035% of bovine serum albumin, pH 7.35) was applied on 10 ml of Sepharose 2B column and eluted with such a buffer to prepare a washed platelet.

The platelet aggregation reaction was measured by an aggregometer (NKK HEMA TRACER 1 MODEL PAT-6A.6M, Niko bioscience). In a measuring cuvette was placed 245 $\mu$l of the washed platelet of which platelet number was adjusted to $5\times10^5/\mu l$ and set in the aggregometer. The washed platelet was stirred (1000 rpm) at 37° C. and 3.8 $\mu$l of 0.1M of $CaCl_2$ was added thereto. One minute later, 0.5 $\mu$l of a solution of a test compound in dimethylsulfoxide was added and 2 minutes later, 1 $\mu$l of collagen (Collagen reagent Horm®, HORMON-CHEMIE Munchen GMBH, final concentrate 4 $\mu$g/ml) as an inducer for platelet aggregating was added. The platelet aggregation was monitored with an aggregometer in terms of the increase and decrease in transmittancy.

Concentration of 50% inhibition was calculated from the inhibitory rate of aggregation (this corresponds to transmittancy of a sample which is measured at 3 minutes after the addition of a platelet aggregation inducer, provided that transmittancies of the washed platelet and the buffer samples are taken as at 0% and 100%, respectively.)

The results of the test are shown in Table 12.

TABLE 12

| Inhibition of Aggregation for Rats Washed Platelet Inducer for Platelet Aggregating: Collagen [4 $\mu$g/ml] | |
|---|---|
| Test* Compound Number | 50% Inhibitory Concentration ($IC_{50}$) [nM] |
| Iaa-b | 3 |
| (+)-Iaa-b | 2 |
| Iab-b | 2 |
| Iac-b | 2 |
| Iad-b | 2 |
| Iae-b | 2 |
| Iba-b | 20 |
| Ica-b | 10 |
| Ida-b | 3 |
| Iea-b | 20 |
| Ieb-b | 4 |
| Iec-b | 2 |
| Iee-b | 5 |
| Ieh-b | 10 |
| Iei-b | 9 |
| Iej-b | 7 |
| Iek-b | 5 |
| Iel-b | 20 |

*Test compound number corresponds to that used in Example.

The objective compounds of this invention show potent inhibitory activities against platelet aggregation caused by collagen.

Experiment 2

Long Acting Inhibitory effect for Guinea Pig Platelet Aggregation (ex vivo)

Material and Method

A solution of test compound in physiological saline was administered (dosage: 0.5 mg/kg, dosage volume: 2 ml/Kg) to a guinea pig (Slc- Hartley, male, 9 weeks old, weight 520 to 590 g).

Inhibitory effect for platelet aggregation was measured in 1, 3, and 6 hours after administration of the test compounds.

Under sodium pentobarbital anesthesia, blood was collected from the abdominal artery in such the ratio that 3.8% sodium citrate solution/blood was 1 volume/9 volume.

The blood centrifuged for 15 minutes at 180×g at 22° C. to give platelet rich plasma (PRP). The remaining blood was further centrifuged at 3,000 rpm for 10 minutes at 22° C. to give platelet-poor plasma (PPP).

The platelet aggregation test was performed according to Born's method [Born, G.V.R., Nature, 194, 927–929 (1962)], using an aggregometer (model AUTO RAM-61, Rika Denki Kogyo CO., Ltd.). 400 $\mu$l of PRP, whose platelets number was prepared to count $50–55\times10^4/\mu l$, was placed in a measuring cuvette and set in the aggregometer. PRP was stirred for 1 minute (at 1,200 rpm) at 37° C. and preliminarily warmed. As an inducer for platelet aggregating, 100 $\mu$l of arachidonic acid (sodium salt, Sigma) was added and the platelet aggregation was monitored with an aggregometer in terms of the increase and decrease in light transmission.

Setting the light transmittance for PRP at 0% of platelet aggregating rate, and that for PPP at 100%, the maximum light transmittance for the sample, after the addition of the inducer for platelet aggregating, was regarded as the maximum platelet aggregation rate.

The inhibitory rate for aggregation (%) was calculated from the ratio of the maximum aggregation rate in the test-compound-added group to that in the control group (carrier-added group).

The results of the test are shown in Table 13. Table 13.

| Time in hours after p.o. Administration | AA (100 μM)-Induced Platelet Aggregation (%) Iaa-b |
|---|---|
| 0 | 89.7 ± 1.4 |
| 1 | 2.5 ± 2.0* |
| 3 | 19.0 ± 18.0* |
| 6 | 56.3 ± 20.4 |

AA; Arachidonic acid
Platelet Aggregation (%) are shown by Mean ± S.E. in 5 guinea pigs.
*statistically significant (p < 0.05)

Compound Iaa-b significantly inhibited arachidonic acid induced platelet aggregation both in 1 and 3 hours after the administration. Its inhibitory effect was still observed in 6 hours after the administration. The compound of the present invention Iaa-b is a long acting compound.

Experiment 3

Protective effects on sodium arachidonate-induced pulmonary thromboembolic death in mice.

Material and Method

The mice (DDY, 4 weeks old, male, weight 20 to 25 g) in a group of ten are used.

Pulmonary thromboembolic death was induced by injecting 99% solution of sodium arachidonate (Sigma) in physiological saline [100 mg/kg (100% pulmonary thromboembolic death was induced in this amount.)] into tail vein. In order to examine the duration time of the test compound, sodium arachidonate was administrated in 15 minutes and 60 minutes after an administration of a solution of the test compounds in physioligical saline into tail vein. The mortality at 1 hour was determined and $ED_{50}$ was calculated by probit method.

The results are shown in Table 14.

TABLE 14

| Compd. No. | Pretreatment (min.) | $ED_{50}$ (95% confidence limit) [mg/Kg] |
|---|---|---|
| Iaa-b | 15 | 1.8 (0.6–6.9) |
|  | 60 | 1.5 (0.9–2.5) |

In 15 minutes and 60 minutes pretreatment of the compound Iaa-b of the present invention did not show significantly different inhibitory potency and its 60 minutes pretreatment showed rather stronger inhibitory effect. Thus, the compound Iaa-b of the present invention is a long-acting compound.

What we claim is:

1. A compound represented by the formula:

$$\underset{H}{\underset{N}{\overset{N}{\diagdown}}}\underset{N}{\overset{N}{\diagup}}-(CH_2)_3CH=CH(CH_2)_n-\underset{\underset{(CH_2)_q}{\underset{X}{\diagdown}\diagup}}{\overset{(CH_2)_p\quad(CH_2)_r}{\diagup\diagdown}}-NHSO_2-R$$

wherein R is naphthyl or phenyl optionally substituted by phenyl, lower alkyl, halogen, lower alkoxy, hydroxy or acetoxy; X is methylene, dimethylmethylene or oxygen; n is an integer of 0 or 1; and p and r each is an integer of 0 or 1 and q is an integer of 1 or 2 provided that $p+q+r=2$; or a tautomer in tetrazole ring and a pharmaceutically acceptable salt thereof.

2. A compound claimed in claim 1 wherein X is methylene, p and r each is an integer of 0 and q is an integer of 2.

3. A compound claimed in claim 1 wherein X is oxygen, p and r each is an integer of 0 and q is an integer of 2.

4. A compound claimed in claim 1 wherein X is dimethylmethylene, n is an integer of 1, p and r each is an integer of 0 or 1 and q is an integer of 1.

5. A compound claimed in claim 1, namely, (1R,2S,3S,4S)-3-phenylsulfonylamino-2-[(2Z)-6-(5-tetrazolyl) hex-2-enyl]bicyclo[2.2.1]heptane.

* * * * *